United States Patent
Henary et al.

(10) Patent No.: US 11,426,404 B2
(45) Date of Patent: Aug. 30, 2022

(54) **DOSING OF *KRAS* INHIBITOR FOR TREATMENT OF CANCERS**

(71) Applicant: AMGEN INC., Thousand Oaks, CA (US)

(72) Inventors: Haby Henary, Moorpark, CA (US); James Russell Lipford, Thousand Oaks, CA (US); Victor J. Cee, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 90 days.

(21) Appl. No.: 15/930,606

(22) Filed: May 13, 2020

(65) Prior Publication Data

US 2020/0360374 A1 Nov. 19, 2020

Related U.S. Application Data

(60) Provisional application No. 62/847,862, filed on May 14, 2019, provisional application No. 62/867,747, filed on Jun. 27, 2019.

(51) Int. Cl.
*A61K 31/505* (2006.01)
*A61P 35/00* (2006.01)
*A61K 9/00* (2006.01)
*A61K 31/53* (2006.01)
*A61K 31/5355* (2006.01)
*A61K 39/00* (2006.01)

(52) U.S. Cl.
CPC ............ *A61K 31/505* (2013.01); *A61P 35/00* (2018.01); *A61K 9/0053* (2013.01); *A61K 31/53* (2013.01); *A61K 31/5355* (2013.01); *A61K 2039/505* (2013.01)

(58) Field of Classification Search
CPC .................................................. A61K 31/505
See application file for complete search history.

(56) References Cited

U.S. PATENT DOCUMENTS

| | | |
|---|---|---|
| 4,232,027 A | 11/1980 | Turk et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,151,413 A | 9/1992 | Caufield et al. |
| 5,256,790 A | 10/1993 | Nelson |
| 5,258,389 A | 11/1993 | Goulet et al. |
| 5,521,184 A | 5/1996 | Zimmermann |
| 5,650,415 A | 7/1997 | Tang et al. |
| 5,656,643 A | 8/1997 | Spada et al. |
| 5,712,291 A | 1/1998 | D'Amato |
| 5,728,813 A | 3/1998 | Lyman et al. |
| 5,747,498 A | 5/1998 | Schnur et al. |
| 5,770,599 A | 6/1998 | Gibson |
| 5,789,427 A | 8/1998 | Chen et al. |
| 5,792,783 A | 8/1998 | Tang et al. |
| 5,861,510 A | 1/1999 | Piscopio et al. |
| 5,863,949 A | 1/1999 | Robinson et al. |
| 5,892,112 A | 4/1999 | Levy et al. |
| 5,969,110 A | 10/1999 | Beckmann et al. |
| 5,981,245 A | 11/1999 | Fox et al. |
| 5,990,141 A | 11/1999 | Hirth et al. |
| 6,057,124 A | 5/2000 | Bartley et al. |
| 6,111,090 A | 8/2000 | Gorman et al. |
| 6,232,447 B1 | 5/2001 | Cerretti |
| 6,235,764 B1 | 5/2001 | Larson et al. |
| 6,258,812 B1 | 7/2001 | Bold et al. |
| 6,413,932 B1 | 7/2002 | Cerretti et al. |
| 6,515,004 B1 | 2/2003 | Misra et al. |
| 6,596,852 B2 | 7/2003 | Cerretti et al. |
| 6,630,500 B2 | 10/2003 | Gingrich et al. |
| 6,656,963 B2 | 12/2003 | Firestone et al. |
| 6,713,485 B2 | 3/2004 | Carter et al. |
| 6,727,225 B2 | 4/2004 | Wiley |
| 7,025,962 B1 | 4/2006 | Gorman et al. |
| 7,361,760 B2 | 4/2008 | Sircar et al. |
| 7,618,632 B2 | 11/2009 | Collins et al. |
| 7,812,135 B2 | 10/2010 | Smith et al. |
| 8,388,967 B2 | 3/2013 | Smith et al. |
| 8,586,023 B2 | 11/2013 | Shiku et al. |
| 8,591,886 B2 | 11/2013 | Ponath et al. |
| 10,519,146 B2 | 12/2019 | Lanman et al. |
| 10,532,042 B2 | 1/2020 | Lanman et al. |
| 10,640,504 B2 | 5/2020 | Lanman et al. |
| 10,988,485 B2 | 4/2021 | Minatti et al. |
| 11,045,484 B2 | 6/2021 | Wurz et al. |
| 11,053,226 B2 | 7/2021 | Shin et al. |
| 11,090,304 B2 | 8/2021 | Allen et al. |
| 11,096,939 B2 | 8/2021 | Booker et al. |
| 11,236,091 B2 | 2/2022 | Chaves et al. |

(Continued)

FOREIGN PATENT DOCUMENTS

DE 19629652 A1 1/1998
EP 0090505 A2 10/1983

(Continued)

OTHER PUBLICATIONS

AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).

AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).

Canon, et al., "The clinical KRAS(G12C) inhibitor AMG 510 drives anti-tumour immunity," *Nature*, 575(7781): 217-223 (2019) (Supplementary Material, pp. 1-55).

(Continued)

*Primary Examiner* — Paul V Ward

(74) *Attorney, Agent, or Firm* — Markus Bergauer

(57) ABSTRACT

Provided herein are methods of administering a KRAS G12C inhibitor to a cancer subject.

47 Claims, 19 Drawing Sheets

(56) References Cited

U.S. PATENT DOCUMENTS

| | | |
|---|---|---|
| 11,285,135 B2 | 3/2022 | Lanman et al. |
| 11,285,156 B2 | 3/2022 | Allen et al. |
| 11,299,491 B2 | 4/2022 | Parsons et al. |
| 11,306,087 B2 | 4/2022 | Lanman et al. |
| 2002/0042368 A1 | 4/2002 | Fanslow, III et al. |
| 2003/0105091 A1 | 6/2003 | Riedl et al. |
| 2003/0162712 A1 | 8/2003 | Cerretti et al. |
| 2009/0012085 A1 | 1/2009 | Baum et al. |
| 2014/0288045 A1 | 9/2014 | Ren et al. |
| 2015/0239900 A1 | 8/2015 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2018/0015087 A1 | 1/2018 | Liu et al. |
| 2018/0072723 A1 | 3/2018 | Blake et al. |
| 2019/0336514 A1 | 11/2019 | Wurz et al. |
| 2019/0343838 A1 | 11/2019 | Allen et al. |
| 2019/0345169 A1 | 11/2019 | Minatti et al. |
| 2019/0374542 A1 | 12/2019 | Allen et al. |
| 2019/0375749 A1 | 12/2019 | Chen et al. |
| 2020/0030324 A1 | 1/2020 | Booker et al. |
| 2020/0055845 A1 | 2/2020 | Lanman et al. |
| 2020/0069657 A1 | 3/2020 | Lanman et al. |
| 2020/0165231 A1 | 5/2020 | Shin et al. |
| 2020/0207766 A1 | 7/2020 | Lanman et al. |
| 2020/0216446 A1 | 7/2020 | Parsons et al. |
| 2020/0222407 A1 | 7/2020 | Lipford et al. |
| 2020/0369662 A1 | 11/2020 | Chaves et al. |
| 2021/0009577 A1 | 1/2021 | Lanman et al. |
| 2022/0002298 A1 | 1/2022 | Chen et al. |

FOREIGN PATENT DOCUMENTS

| | | |
|---|---|---|
| EP | 0520722 A1 | 12/1992 |
| EP | 0566226 A1 | 10/1993 |
| EP | 0606046 A1 | 7/1994 |
| EP | 0682027 A1 | 11/1995 |
| EP | 0407122 A1 | 10/1996 |
| EP | 0770622 A2 | 5/1997 |
| EP | 0780386 A1 | 6/1997 |
| EP | 0787772 A2 | 8/1997 |
| EP | 0818442 A2 | 1/1998 |
| EP | 0837063 A1 | 4/1998 |
| EP | 0931788 A2 | 7/1998 |
| EP | 0970070 B1 | 1/2000 |
| EP | 1004578 A2 | 5/2000 |
| EP | 1181017 B1 | 2/2002 |
| EP | 1786785 B9 | 5/2007 |
| EP | 1866339 B1 | 12/2007 |
| EP | 1947183 A1 | 7/2008 |
| EP | 3401314 A1 | 11/2019 |
| EP | 3055290 B1 | 12/2019 |
| JP | 02233610 A | 9/1990 |
| JP | 2019031476 A | 2/2019 |
| WO | 1990005719 A1 | 5/1990 |
| WO | 1992005179 A1 | 4/1992 |
| WO | 1992020642 A1 | 11/1992 |
| WO | 1993011130 A1 | 6/1993 |
| WO | 1994002136 A1 | 2/1994 |
| WO | 1994002485 A1 | 2/1994 |
| WO | 1994009010 A1 | 4/1994 |
| WO | 1995009847 A1 | 4/1995 |
| WO | 1995014023 A1 | 5/1995 |
| WO | 1995016691 A1 | 6/1995 |
| WO | 1995019774 A1 | 7/1995 |
| WO | 1995019970 A1 | 7/1995 |
| WO | 1996027583 A1 | 9/1996 |
| WO | 1996030347 A1 | 10/1996 |
| WO | 1996031510 A1 | 10/1996 |
| WO | 1996033172 A1 | 10/1996 |
| WO | 1996033980 A1 | 10/1996 |
| WO | 1996041807 A1 | 12/1996 |
| WO | 1997002266 A1 | 1/1997 |
| WO | 1997013771 A1 | 4/1997 |
| WO | 1997019065 A1 | 5/1997 |
| WO | 1997027199 A1 | 7/1997 |
| WO | 1997030034 A1 | 8/1997 |
| WO | 1997030044 A1 | 8/1997 |
| WO | 1997032880 A1 | 9/1997 |
| WO | 1997032881 A1 | 9/1997 |
| WO | 1997034895 A1 | 9/1997 |
| WO | 1997038983 A1 | 10/1997 |
| WO | 1997038994 A1 | 10/1997 |
| WO | 1997049688 A1 | 12/1997 |
| WO | 1998002434 A1 | 1/1998 |
| WO | 1998002437 A1 | 1/1998 |
| WO | 1998002438 A1 | 1/1998 |
| WO | 1998002441 A2 | 1/1998 |
| WO | 1998003516 A1 | 1/1998 |
| WO | 1998007697 A1 | 2/1998 |
| WO | 1998007726 A1 | 2/1998 |
| WO | 1998014449 A1 | 4/1998 |
| WO | 1998014450 A1 | 4/1998 |
| WO | 1998014451 A1 | 4/1998 |
| WO | 1998017662 A1 | 4/1998 |
| WO | 1998034918 A1 | 4/1998 |
| WO | 1998030566 A1 | 7/1998 |
| WO | 1998033768 A1 | 8/1998 |
| WO | 1998033798 A2 | 8/1998 |
| WO | 1998034915 A1 | 8/1998 |
| WO | 1999007675 A1 | 2/1999 |
| WO | 1999007701 A1 | 2/1999 |
| WO | 1999020758 A1 | 4/1999 |
| WO | 1999029667 A1 | 6/1999 |
| WO | 1999035132 A1 | 7/1999 |
| WO | 1999035146 A1 | 7/1999 |
| WO | 1999040196 A1 | 8/1999 |
| WO | 1999045009 A1 | 9/1999 |
| WO | 1999052889 A1 | 10/1999 |
| WO | 1999052910 A1 | 10/1999 |
| WO | 1999061422 A1 | 12/1999 |
| WO | 2000002871 A1 | 1/2000 |
| WO | 2000012089 A1 | 3/2000 |
| WO | 2000059509 A1 | 10/2000 |
| WO | 2001003720 A2 | 1/2001 |
| WO | 2001014387 A1 | 3/2001 |
| WO | 2001032651 A1 | 5/2001 |
| WO | 2001037820 A2 | 5/2001 |
| WO | 2002055501 A2 | 7/2002 |
| WO | 2002059110 A1 | 8/2002 |
| WO | 2002066470 A1 | 8/2002 |
| WO | 2002068406 A2 | 9/2002 |
| WO | 2004005279 A2 | 1/2004 |
| WO | 2004007458 A1 | 1/2004 |
| WO | 2004007481 A2 | 1/2004 |
| WO | 2004009784 A2 | 1/2004 |
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2009036082 A2 | 3/2009 |
| WO | 2009055730 A1 | 4/2009 |
| WO | 2010003118 A1 | 1/2010 |
| WO | 2010149786 A1 | 12/2010 |
| WO | 2011028683 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |

(56) References Cited

FOREIGN PATENT DOCUMENTS

| WO | 2016044772 A1 | 3/2016 |
|---|---|---|
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020102730 A1 | 5/2020 |
| WO | 2020106640 A1 | 5/2020 |
| WO | 2020232130 A1 | 11/2020 |
| WO | 2020236947 A1 | 11/2020 |
| WO | 2020236948 A1 | 11/2020 |
| WO | 2021081212 A1 | 4/2021 |
| WO | 2021097207 A1 | 5/2021 |
| WO | 2021097212 A1 | 5/2021 |
| WO | 2021126816 A1 | 6/2021 |
| WO | 2021236920 A1 | 11/2021 |

OTHER PUBLICATIONS

Database Registry [Online], Chemical Abstracts Service, Columbus, Ohio, US; Jul. 31, 2017 (Jul. 31, 2017), XP002801805, retrieved from STN Database accession No. 2105944-09-8.

Final Office Action for U.S. Appl. No. 16/436,647, dated Mar. 24, 2021, 7 pages.

Meanwell, "Synopsis of Some Recent Tactical Application of Bioisosteres in Drug Design," *J. Med. Chem.* 54:2529-2591 (2011).

Non-Final Office Action for U.S. Appl. No. 16/675,121, dated Feb. 2, 2021, 10 pages.

Non-Final Office Action for U.S. Appl. No. 16/817,109, dated Mar. 3, 2021, 12 pages.

Notice of Allowance dated Jan. 14, 2021 for U.S. Appl. No. 16/402,589, 5 pages.

Notice of Allowance, dated Dec. 21, 2020, for U.S. Appl. No. 16/407,889, 5 pages.

Notice of Allowance, dated Feb. 18, 2021, for U.S. Appl. No. 16/687,546, 9 pages.

Notice of Allowance, dated Jan. 26, 2021, for U.S. Appl. No. 16/438,349, 9 pages.

Notice of Allowance, dated Jan. 27, 2021, for U.S. Appl. No. 16/428,163, 9 pages.

Notice of Allowance, dated Mar. 30, 2021, for U.S. Appl. No. 16/402,538, 8 pages.

Shibata et al., "A Convenient Synthesis of 3-Cyano-2-methylpyridines under Ultrasonic Irradiation," *Bull. Chem. Soc. Jpn.*, 61:2199-2200 (1988).

Stanetty et al., "Synthesis of Aza Analogs of the Herbicide Sindone B," *Monatshefte Fuer Chemie*, 130:441-450 (1999).

Third Party Observation filed for PCT/US2020/033831, submitted Jan. 15, 2021, 2 pages.

4-methyl-2-(1-methylethyl)-3-Pyridinamine, STN Registry, CAS RN 1698293-93-4, STN entry date May 5, 2015 (May 5, 2015).

Amgen Press Release, "Amgen Announces New Clinical Data Evaluating Novel Investigational KRAS(G12C) Inhibitor in Larger Patient Group At WCLC 2019," dated Sep. 8, 2019 (last accessed Apr. 13, 2021).

Govindan et al., "OA01.06 Safety, Efficacy, and Pharmacokinetics of AMG 510, a Novel $KRAS^{G12C}$ Inhibitor, in Patients with Non-Small Cell Lung Cancer," *J. Thorac. Oncol.*, 14(11, Supplement 1):S1125-1126 (Nov. 2019).

Hirayama, "Handbook for Making Crystal of Organic Compound,—Principles and Know-how—", Maruzen Co., Ltd., Jul. 25, 2008, pp. 57-84 (incl. English translation).

International Search Report for PCT/US2020/056874, dated Feb. 12, 2021, 7 pages.

International Search Report for PCT/US2020/060415, dated Feb. 3, 2021, 7 pages.

International Search Report for PCT/US2020/065050, dated Mar. 29, 2021, 7 pages.

Kojima, "Aiming to Improve the Efficiency of Crystallization Selection in Drug Development", Pharmaceutics, Sep. 1, 2008, vol. 68, No. 5, pp. 344-349 (incl. English translation).

Noriyuki, "API Form Screening and Selection at the Drug Discovery Stage", Pharm Stage, vol. 6, No. 10, Jan. 15, 2007, pp. 20-25 (incl. English translation).

Notice of Allowance, dated Oct. 20, 2021, for U.S. Appl. No. 16/438,349, 9 pages.

Notice of Allowance, dated Sep. 22, 2021, for U.S. Appl. No. 16/878,824, 8 pages.

Notice of Allowance, dated Sep. 9, 2021, for U.S. Appl. No. 16/675,121, 7 pages.

PubChem CID 108190520, 2-isopropyl-4-methylpyridin-3-amine, available at https://pubchem.ncbi.nlm.nih.gov/compound/108190520 (last accessed Aug. 30, 2021).

Written Opinion for PCT/US2020/056874, dated Feb. 12, 2021, 10 pages.

Written Opinion for PCT/US2020/060415, dated Feb. 3, 2021, 9 pages.

Written Opinion for PCT/US2020/065050, dated Mar. 29, 2021, 8 pages.

"A Phase 1, Study Evaluating the Safety, Tolerability, PK, and Efficacy of AMG 510 in Subjects With Solid Tumors With a S Mutation." NCT03600883, comparison of version submitted Apr. 3, 2019 and May 6, 2020 (update posted May 7, 2020), for full history of change see https://clinicaltrials.gov/ct2/history/NCT03600883 (last accessed Nov. 11, 2020), pp. 1-21.

"Acute Leukemia," *The Merck Manual* (Online Edition), pp. 1-6 (2013).

"KRASG12C Inhibitor," Mirati Therapeutics, retrieved on Nov. 27, 2018, from https://www.mirati.com/mrtx849/, 5 pages.

Ahmadian, et al., "Guanosine triphosphatase stimulation of oncogenic Ras mutants," *PNAS*, 96: 7065-7070, 1999.

Airoldi, et al., "Glucose-Derived Ras Pathway Inhibitors: Evidence of Ras-Ligand Binding and Ras-Gef (Cdc25) Interaction Inhibition," *ChemBioChem*, 8: 1376-1379 (2007).

ATTC "Organism: *Mus musculus* (B cell); *Mus musculus* (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.

Barnett, et al., "Identification and characterization of pleckstrin-holomogy-domain-dependent and isoenzyme specific Akt inhibitors," *Biochem. J.*, 385 (2): 399-408 (2005).

Bhatia, et al., "A Review on Bioisosterism: A Rational Approach for Drug Design and Molecular Modification," *Pharmacologyonline*, 1:272-299 (2011).

Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).

(56) References Cited

OTHER PUBLICATIONS

Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).

Canon, et al., "The clinical KRAS(G12C) inhibitor AMG 510 drives anti-tumour immunity," *Nature*, 575(7781): 217-223 (2019).

Cee, et al.,"Discovery of AMG 510, a first-in-humancovalent inhibitor of KRAS$^{G12C}$ for the treatment of solid tumors," Abstract and Presentation, ACS Spring Meeting, Orlando, FL, USA, Mar. 31-Apr. 4, 2019.

Cohen, "The development and therapeutic potential of protein kinase inhibitors," *Current Opinion in Chemical Biology*, 3:459-465 (1999).

Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).

Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).

Dermer, et al., "Another Anniversary for the War on Cancer," *Bio/Technology*, 12: 320 (1994).

Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).

Erkkilä, et al., "Mild Organocatalytic α-Methylenation of Aldehydes," *J. Org. Chem.*, 71 (6), 2538-2541 (2006).

Extended European Search Report for European Patent Application No. 19208193.2, dated Jun. 3, 2020, pp. 1-8.

Fakih, et al., "Phase 1 study evaluating the safety, tolerability, pharmacokinetics (PK), and efficacy of AMG 510, a novel small molecule KRASG12C inhibitor, in advanced solid tumors," *Journal of Clinical Oncology*, 37(15 suppl) (May 20, 2019) 3003, published online May 26, 2019.

Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.

Final Office Action for U.S. Appl. No. 15/984,855, dated Mar. 28, 2019, 7 pages.

Final Office Action for U.S. Appl. No. 16/661,907, dated Mar. 27, 2020, 29 pages.

Freshney, et al., Culture of Animal Cells, *A Manual of Basic Technique*, Alan R. Liss, Inc, New York, p. 4 (1983).

Gentile, et al., "Discovery and Structural Investigation of Novel Binders to the Ras Switch II Pocket," NCI Initiative Symposium Poster (2015).

Gills and Dennis, "The development of phosphatidylinositol ether lipid analogues as inhibitors of the serine/threonine kinase, Akt," *Expert. Opin. Investig. Drugs*, 13: 787-797 (2004).

Goldberg, et al., "Role of PD-1 and its ligand, B7-H1, in early fate decisions of CD8 T cells," *Blood*,110(1): 186-192 (2007).

Goldstein, et al., "Biological efficacy of a chimeric antibody to the epidermal growth factor receptor in a human tumor xenograft model," *Clin. Cancer Res.*, 1: 1311-1318 (1995).

Golub, et al., "Molecular Classification of Cancer: Class Discovery and Class Prediction by Gene Expression Monitoring," *Science*, 286: 531-537(1999).

Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.

Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.

Govindan, et al., "Phase 1 Study of AMG 510, a Novel KRAS G12C Inhibitor, in Advanced Solid Tumors with Kras p.G12C Mutation," Poster, ESMO Congress, Barcelona, Spain, Sep. 27, 2019-Oct. 1, 2019.

Govindan, et al., "Phase 1 Study of Safety, Tolerability, Pharmacokinetics, and Efficacy of AMG510, a Novel KRASG12C Inhibitor, in Non-Small Cell Lung Cancer," Abstract and Presentation, World Conference on Lung Cancer (WCLC), Barcelona, Spain, Sep. 7-10, 2019.

Gura, "Cancer Models: Systems for Identifying New Drugs Are Often Faulty," *Science*, 278(5340):1041-1042 (1997).

Halford, "Amgen unveils its Kras covalent inhibitor AMG 510," *Chemical & Engineering News* 97(14):4 (2019).

Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).

Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).

Hichri, et al., "A Convenient Synthesis of 1,3,2-Benzodiazaphophorine-2-Oxide," *Phosphorus, Sulfur, and Silicon*, 190: 29-35 (2015).

Hichri, et al., CAPLUS Abstract, 162:245378 (2015).

Hocker, et al., "Andrographolide derivatives inhibit guanine nucleotide exchange and abrogate oncogenic Ras function," *PNAS*, 110(25): 10201-10206 (2013).

Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).

International Search Report for PCT/US2017/067801, dated Jul. 25, 2018, 6 pages.

International Search Report for PCT/US2018/033714, dated Jul. 17, 2018, 3 pages.

International Search Report for PCT/US2018/050044, dated Oct. 30, 2018, 7 pages.

International Search Report for PCT/US2019/030593, dated Aug. 6, 2019, 4 pages.

International Search Report for PCT/US2019/030606, dated Jul. 23, 2019, 5 pages.

International Search Report for PCT/US2019/031535, dated Jul. 25, 2019, 7 pages.

International Search Report for PCT/US2019/034974, dated Aug. 9, 2019, 5 pages.

International Search Report for PCT/US2019/036397, dated Aug. 26, 2019, 5 pages.

International Search Report for PCT/US2019/036626, dated Jun. 2, 2020, 5 pages.

International Search Report for PCT/US2019/061815, dated Mar. 5, 2020, 6 pages.

International Search Report for PCT/US2019/062051, dated Mar. 2, 2020, 3 pages.

International Search Report for PCT/US2020/032686, dated Aug. 14, 2020, 4 pages.

International Search Report for PCT/US2020/033831, dated Jul. 9, 2020, 6 pages.

International Search Report for PCT/US2020/033832, dated Jul. 8, 2020, 4 pages.

Janes, et al., "Targeting KRAS Mutant Cancers with a Covalent G12C-Specific Inhibitor," *Cell*, 172: 578-589 (2018).

Jarvis, "Notorious KRAS: Taking down cancer researchers' biggest foe," *Chemical & Engineering News*, 97(37), 9 pages (2019).

Jin, et al., "Inhibition of AKT survival pathway by a small molecule inhibitor in human endometrial cancer cells," *Br. J. Cancer*, 91: 1808-1812 (2004).

Johnson et al., "Relationships between drug activity in NCI preclinical in vitro and in vivo models and early clinical trials," *British Journal of Cancer*, 84(10): 1424-1431 (2001).

Lanivian, et al., "Abstract 4455: Discovery of AMG 510, a first-in-human covalent inhibitor of KRAS$^{G12C}$ for the treatment of solid tumors," Presentation, American Association for Cancer Research (AACR) Annual Meeting, Atlanta, GA, USA, Mar. 29-Apr. 3, 2019.

(56) References Cited

OTHER PUBLICATIONS

Lanman, et al., "Abstract 4455: Discovery of AMG 510, a first-in-human covalent inhibitor of KRAS$^{G12C}$ for the treatment of solid tumors," Proceedings of the American Association for Cancer Research Annual Meeting 2019; Mar. 29-Apr. 3, 2019; Atlanta, GA, USA, AACR, *Cancer Res.* 79(13 Suppl): Abstract nr 4455 (2019).

Lanman, et al., "Discovery of a Covalent Inhibitor of KRAS$^{G12C}$ (AMG 510) for the Treatment of Solid Tumors," *J. Med. Chem.*, 63: 52-65 (2020).

Li et al., "Targeting Protein-Protein Interaction with Covalent Small-Molecule Inhibitors," *Current Topics in Medicinal Chemistry*, 19(21): 1872-1876 (2019).

Lim, et al., "Therapeutic Targeting of Oncogenic K-Ras by a Covalent Catalytic Site Inhibitor," *Angew. Chem. Int. Ed*, 53: 199-204 (2014).

Lipford, et al., "Pre-Clinical Development of AMG 510: The First Inhibitor of KRAS$^{G12C}$ in Clinical Testing," Presentation, American Association for Cancer Research (AACR) Annual Meeting, Atlanta, GA, USA, Mar. 29-Apr. 3, 2019.

Liu, Y., "Session SY28—Transformative Small Molecule Therapies—Targeting KRAS mutant cancers with a covalent G12C-specific inhibitor," Presentation on Apr. 4, 2017, AACR Annual Meeting Presentation, Apr. 1-5, 2017, Washington, D.C. (2017).

Lopez, et al., "Optimization of quinazolinone-based covalent inhibitors of KRAS$^{G12C}$ in the discovery of AMG 510," Abstract and Poster, ACS Fall Meeting, San Diego, CA, USA, Aug. 25-29, 2019.

Lu, et al., "KRAS G12C Drug Development: Discrimination between Switch II Pocket Configurations Using Hydrogen/Deuterium-Exchange Mass Spectrometry," *Structure*, 25: 1-7 (2017).

Maurer, et al., "Small-molecule ligands bind to a distinct pocket in Rad and inhibit SOS-mediated nucleotide exchange activity," *PNAS*, 109(14): 5299-5304 (2012).

Mcgregor, et al., "Expanding the Scope of Electrophiles Capable of Targeting K-Ras Oncogenes," *ACS Bio. Chem.*, 56: 3179-3183 (2017).

Mirati Therapeutics, "Corporate Presentation Nov. 2017," Slides 1-41 (2017).

Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).

Morrissey et al., "Immunotherapy and Novel Combinations in Oncology: Current Landscape, Challenges, and Opportunities," *Clin. Transl. Sci.*, 9(2):89-104 (2016).

National Cancer Institute identifier: NSC 154020, retrieved on Nov. 29, 2018, from https://cactus.nci.nih.gov/ncidb2.2/.

Ncbi Reference Sequence, "GTPase KRas isoform a [*Homo sapiens*]," GenBank Accession No. NM 203524.1, Retrieved on Nov. 29, 2018 from https://www.ncbi.nlm.nih.gov/protein/15718763?sat=4&satkey=234448549, 4 pages.

Non-Final Office Action (Corrected) for U.S. Appl. No. 16/125,359, dated Apr. 8, 2019, 13 pages.

Non-Final Office Action for U.S. Appl. No. 15/849,905, dated Mar. 20, 2019, 18 pages.

Non-Final Office Action for U.S. Appl. No. 15/984,855, dated Sep. 27, 2018, 25 pages.

Non-Final Office Action for U.S. Appl. No. 16/125,359, dated Apr. 5, 2019, 13 pages.

Non-Final Office Action for U.S. Appl. No. 16/402,538, dated Oct. 30, 2019, 12 pages.

Non-Final Office Action for U.S. Appl. No. 16/402,589, dated Mar. 6, 2020, 17 pages.

Non-Final Office Action for U.S. Appl. No. 16/407,889, dated Jul. 1, 2020, 6 pages.

Non-Final Office Action for U.S. Appl. No. 16/428,163, dated Sep. 15, 2020, 6 pages.

Non-Final Office Action for U.S. Appl. No. 16/436,647, dated Aug. 7, 2020, 19 pages.

Non-Final Office Action for U.S. Appl. No. 16/438,349, dated Dec. 13, 2019, 15 pages.

Non-Final Office Action for U.S. Appl. No. 16/661,907, dated Nov. 18, 2019, 20 pages.

Notice of Allowance dated Jul. 24, 2020 for U.S. Appl. No. 16/402,538, 8 pages.

Notice of Allowance dated Sep. 16, 2020 for U.S. Appl. No. 16/402,589, 5 pages.

Notice of Allowance dated Sep. 9, 2020 for U.S. Appl. No. 16/438,349, 9 pages.

Ostrem, et al., "Development of mutant-specific small molecule inhibitors of K-Ras," Poster, AACR 104th Annual Meeting 2013; Apr. 6-10, 2013; Washington, D.C. (2013).

Ostrem, et al., "K-Ras(G12C) inhibitors allosterically control GTP affinity and effector interactions," *Nature*, 503: 548-551 (2013).

Paez, et al., "*EGFR* Mutations in Lung Cancer Correlation with Clinical Response to Gefitinib Therapy," *Science*, 304(5676): 1497-500 (2004).

Palmioli, et al., "First experimental identification of Ras-inhibitor binding interface using a water-soluble Ras ligand," *Bioorg. Med. Chem. Lett.*, 19: 4217-4222 (2009).

Patricelli, et al., "Selective Inhibition of Oncogenic KRAS Output with Small Molecules Targeting the Inactive State," *Cancer Discov*, 6 (3): 316-329 (2016).

Pearce, et al., "Failure modes in anticancer drug discovery and development," *Cancer Drug Design and Discovery*, Edited by Stephen Neidle, Chapter 18, pp. 424-435 (2008).

Peri, et al., "Design, Synthesis and Biological Evaluation of Sugar-Derived Ras Inhibitors," *ChemBioChem*, 6: 1839-1848 (2005).

Peri, et al., "Sugar-Derived Ras Inhibitors: Group Epitope Mapping by NMR Spectroscopy and Biological Evaluation," *Eur. J. Org. Chem.*, 16: 3707-3720 (2006).

Peters, et al., "Selective inhibition of K-Ras G12C through allosteric control of GTP affinity and effector interactions," EORTC Poster (2013).

Remington's Pharmaceutical Sciences, 1435-1712 (18th ed., Mack Publishing Co, Easton, Pennsylvania, 1990 (Table of Contents Only).

Rex et al., "KRAS-AACR 2018," Amgen Collection of Information published at Proceedings of the American Association for Cancer Research Annual Meeting 2018; Apr. 14-18, 2018; Chicago, IL; AACR; slides 1-24 (2018).

Rex, et al., "Abstract 3090: In vivo characterization of AMG 510—a potent and selective KRAS$^{G12C}$ covalent small molecule inhibitor in preclinical KRAS$^{G12C}$ cancer models," Poster, American Association for Cancer Research (AACR) Annual Meeting, Atlanta, GA, USA, Mar. 29-Apr. 3, 2019.

Rex, et al., "Abstract 3090: In vivo characterization of AMG 510—a potent and selective KRAS$^{G12C}$ covalent small molecule inhibitor in preclinical KRAS$^{G12C}$ cancer models," Proceedings of the American Association for Cancer Research Annual Meeting 2019; Mar. 29-Apr. 3, 2019; Atlanta, GA, USA, AACR, *Cancer Res.* 79(13 Suppl): Abstract nr 3090 (2019).

Saiki, et al., "Abstract 4484: Discovery and in vitro characterization of AMG 510—a potent and selective covalent small-molecule inhibitor of KRAS$^{G12C}$," Presentation, American Association for Cancer Research (AACR) Annual Meeting, Atlanta, GA, USA, Mar. 29-Apr. 3, 2019.

Saiki, et al., "Abstract 4484: Discovery and in vitro characterization of AMG 510—a potent and selective covalent small-molecule inhibitor of KRAS$^{G12C}$," Proceedings of the American Association for Cancer Research Annual Meeting 2019; Mar. 29-Apr. 3, 2019; Atlanta, GA, USA, AACR, *Cancer Res.* 79(13 Suppl): Abstract nr 4484 (2019).

Sarkar, et al., "Indole-3-Carbinol and Prostate Cancer[1,2]," *J. Nutr.*, 134(12 Suppl): 3493S-3498S (2004).

Shima, et al., "In silico discovery of small-molecule Ras inhibitors that display antitumor activity by blocking the Ras-effector interaction," *PNAS*, 110(20): 8182-8187 (2013).

Simone, "Part XIV Oncology: Introduction," *Cecil Textbook of Medicine*, 20$^{th}$ Edition, 1:1004-1010 (1996).

Singh, et al., "Improving Prospects for Targeting RAS," *J. Clinc. Oncl*, 33(31): 3650-3660 (2015).

Statsyuk, "Let K-Ras activate its own inhibitor," *Nature Structural & Molecular Biology*, 25:435-439 (2018).

(56) References Cited

OTHER PUBLICATIONS

Sun, et al., "Discovery of Small Molecules that Bind to K-Ras and Inhibit Sos-Mediated Activation," *Angew. Chem. Int. Ed.*, 51: 6140-6143 (2012).
Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.*,, 5(1): 125-133 (1997).
Teramoto, et al., 1996, Cancer 77 (4):639-645.
The ASCO Post Staff, "AACR-NCI-EORTC: Investigational KRAS G12C Inhibitor for KRAS-Mutant Solid Tumors," The ASCO Post (2019).
Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).
Traxler, "Tyrosine kinase inhibitors in cancer treatment (Part II)," *Exp. Opin. Ther. Patents*, 8(12): 1599-1625 (1998).
U.S. Appl. No. 60/528,340, filed Dec. 9, 2003.
Wang, et al., "Ras inhibition via direct Ras binding—is there a path forward?," *Bioorg. Med. Chem. Lett.*, 22: 5766-5776 (2012).
Written Opinion for PCT/US2017/067801, dated Jul. 25, 2018, 10 pages.
Written Opinion for PCT/US2018/033714, dated Jul. 17, 2018, 5 pages.
Written Opinion for PCT/US2018/050044, dated Oct. 30, 2018, 7 pages.
Written Opinion for PCT/US2019/030593, dated Aug. 6, 2019, 5 pages.
Written Opinion for PCT/US2019/030606, dated Jul. 23, 2019, 6 pages.
Written Opinion for PCT/US2019/031535, dated Jul. 25, 2019, 7 pages.
Written Opinion for PCT/US2019/034974, dated Aug. 9, 2019, 5 pages.
Written Opinion for PCT/US2019/036397, dated Aug. 26, 2019, 5 pages.
Written Opinion for PCT/US2019/036626, dated Jun. 2, 2020, 12 pages.
Written Opinion for PCT/US2019/061815, dated Mar. 5, 2020, 4 pages.
Written Opinion for PCT/US2019/062051, dated Mar. 2, 2020, 5 pages.
Written Opinion for PCT/US2020/032686, dated Aug. 14, 2020, 6 pages.
Written Opinion for PCT/US2020/033831, dated Jul. 9, 2020, 7 pages.
Written Opinion for PCT/US2020/033832, dated Jul. 8, 2020, 6 pages.
Xiong, et al., "Covalent Guanosine Mimetic Inhibitors of G12C KRAS," *ACS Med. Chem. Lett.*, 8: 61-66 (2017).
Yan, et al., "Pharmacogenetics and pharmacogenomics in oncology therapeutic antibody development," *BioTechniques*, 29(4): 565-568 (2005).
Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).
Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).
Zeng, et al., "Potent and Selective Covalent Quinazoline Inhibitors of KRAS G12C," *Cell Chemical Biology*, 24: 1-12 (2017).
Zimmerman, et al., "Small molecule inhibition of the KRAS-PDEδ interaction impairs oncogenic KRAS signaling," *Nature*, 1-5 (2017).
Aggarwal, et al., "Clinicopathological characteristics and treatment patterns observed in real-world care in patients with advanced non-small cell lung cancer(NSCLC) and *KRAS* G12C mutationsin the Flatiron Health (FH)—Foundation Medicine (FMI) Clinico-Genomic Database (CGDB)," Abstract and Presentation, ESMO Virtual Congress, Sep. 19-21, 2020.
Durm, et al., "Durability of clinical benefit and biomarkers in patients with advanced non-small cell lung cancer (NSCLC) treated with AMG 510 (sotorasib): CodeBreaK 100," Presentation, North America Conference on Lung Cancer (NACLC), Virtual Worldwide Event, Oct. 16-17, 2020.
Fakih, et al., "CodeBreak 100: Activity of AMG 510, a novel small molecule inhibitor of KRAS$^{G12C}$, in patients with advanced colorectal cancer," Abstract and Poster, ASCO Virtual Meeting, May 29-31, 2020.
Fakih, et al.,"Trial in progress: A phase 1b study of AMG510, a specific and irreversible KRAS$^{G12C}$ inhibitor, in combination withother anticancer therapies in patients with advanced solid tumorsharboring KRASp.G12C mutation (CodeBreak™ 101Trial)," Abstract and Poster, ASCO Virtual Meeting, May 29-31, 2020.
Falchook, et al., "Trial in Progress: A Phase 1b Study of Sotorasib (AMG510), a Specific and Irreversible KRAS$^{G12C}$ Inhibitor, in Combination With OtherAnticancer Therapies in Patients With Advanced Solid Tumors Harboring *KRAS* p.G12C Mutation (CodeBreak101)," Presentation, North America Conference on Lung Cancer (NACLC), Virtual Worldwide Event, Oct. 16-17, 2020.
Hong, et al., "Durability of clinical benefit and biomarkers in patients with advanced non-small cell lung cancer (NSCLC) treated with AMG 510 (sotorasib): CodeBreaK 100," Abstract and Presentation, ESMO Virtual Congress, Sep. 19-21, 2020.
Hong, et al.,"CodeBreak 100: Phase 1 study of AMG 510, a novel KRAS$^{G12C}$ inhibitor, in patients (pts) with advanced solid tumors other than non-small-cell lung cancer (NSCLC) and colorectal cancer (CRC)," Abstract and Poster, ASCO Virtual Meeting, May 29-31, 2020.
Hong, et al.,"KRAS$^{G12C}$ Inhibition with Sotorasib in Advanced Solid Tumors," *N. Engl. Med.*, 383:1207-1217 (2020).
Reck, et al., "CodeBreak 200: a phase 3 multicenter study of sotorasib (AMG 510), a KRAS(G12C) inhibitor, versus docetaxel in patients with previously treated advanced non-small cell lung cancer (NSCLC) harboring KRAS p.G12C mutation," Abstract and Presentation, ESMO Virtual Congress, Sep. 19-21, 2020.
Scharpf, et al., "Comprehensive Pan-Cancer Analyses of RAS Genomic Diversity," Abstract and Presentation, American Association for Cancer Research (AACR) Annual Meeting, Apr. 24-29, 2020.
Spira, et al., "CodeBreak 200: A phase 3 multicenter study of sotorasib (AMG 510), a KRAS(G12C) inhibitor, versus docetaxel in patients with previously treated advanced non-small cell lung cancer (NSCLC) harboring KRAS p.G12C mutation," Presentation, North America Conference on Lung Cancer (NACLC), Virtual Worldwide Event, Oct. 16-17, 2020.
Strickler, et al., "AMG 510, a novel small molecule inhibitor of KRAS G12C, for patients with advanced gastrointestinal cancers: Results from the CodeBreak 100 phase 1 trial," Abstract and Presentation, World Congress on Gastrointestinal Cancer, Virtual Meeting, Jul. 1-4, 2020 (abstract available as of Jul. 1, 2020).
International Search Report for PCT/US2019/62064, dated Oct. 29, 2020, 9 pages.
Written Opinion for PCT/US2019/62064, dated Oct. 29, 2020, 13 pages.
"A Phase 1b Protocol AMG 510 Activity in Subjects With Advanced Solid Tumors With KRAS p.G12C Mutation (CodeBreak 101)." NCT04185883, comparison of version submitted Dec. 3, 2019 and Apr. 3, 2020 (update posted Apr. 7, 2020), for full history of change see https://clinicaltrials.gov/ct2/history/NCT04185883 (last accessed Nov. 11, 2020), pp. 1-11.
"Study to Compare AMG 510 "Proposed INN Sotorasib" With Docetaxel in Non Small Cell Lung Cancer (NSCLC) (CodeBreak 200)" NCT04303780, comparison of version submitted Mar. 9, 2020 and Apr. 22, 2020 (update posted Apr. 24, 2020), for full history of change see https://clinicaltrials.gov/ct2/history/NCT04303780 (last accessed Nov. 11, 2020), pp. 1-9.
Examiner-Initiated Interview Summary, dated Dec. 9, 2021, for U.S. Appl. No. 16/817,109, 1 page.
International Search Report for PCT/US2020/060421, dated Feb. 18, 2021, 4 pages.

(56) References Cited

OTHER PUBLICATIONS

Notice of Allowance, dated Dec. 9, 2021, for U.S. Appl. No. 16/817,109, 9 pages.
Notice of Allowance, dated Dec. 9, 2021, for U.S. Appl. No. 16/685,841, 8 pages.
Notice of Allowance, dated Nov. 1, 2021, for U.S. Appl. No. 16/675,121, 7 pages.
Office Communication (Ex Parte Quayle) for U.S. Appl. No. 16/687,563, dated Jan. 14, 2022, 5 pages.
Written Opinion for PCT/US2020/060421, dated Feb. 18, 2021, 5 pages.

DOSING OF *KRAS* INHIBITOR FOR TREATMENT OF CANCERS

CROSS REFERENCES TO RELATED APPLICATIONS

This application claims the benefit of U.S. Provisional Application No. 62/847,862, filed on May 14, 2019 and U.S. Provisional Application No. 62/867,747, filed on Jun. 27, 2019, which are both hereby incorporated by reference in their entirety and for all purposes as if fully set forth herein.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation and including those who have progressed after chemotherapy. Oncogenic KRAS mutations at residues G12, G13, and Q61 represent the most common RAS mutations found in solid malignancies. Recently it has been demonstrated that $KRAS^{G12C}$ can be targeted with covalent small molecule inhibitors which react with the mutant cysteine adjacent to the switch II pocket (SIIP), locking KRAS in its inactive GDP-bound state.

KRAS is the most frequently mutated oncogene in human cancer and encodes a key signaling protein in tumors. The $KRAS^{G12C}$ mutant harbors a cysteine that has been exploited to design covalent inhibitors with promising preclinical activity. We optimized a series of inhibitors with novel binding interactions and markedly enhanced potency and selectivity. These efforts led to the discovery of AMG 510 (also referred to as Compound A herein), the first $KRAS^{G12C}$ inhibitor in clinical development. Preclinically AMG 510 treatment regressed KRAS p.G12C tumors and significantly improved the anti-tumor efficacy of chemotherapy and targeted agents. In immune-competent mice, AMG 510 treatment resulted in a pro-inflammatory tumor microenvironment and produced durable cures in combination with immune checkpoint inhibition. Cured mice rejected the growth of isogenic KRAS p.G12D tumors, suggesting adaptive immunity against shared antigens. AMG 510 demonstrated preliminary evidence of clinical anti-tumor activity in the first dosing cohort and represents a potentially transformative therapy for patients lacking effective treatments.

The KRAS oncoprotein is a GTPase that is an essential mediator of intracellular signaling pathways involved in tumor cell growth and survival. In normal cells, KRAS functions as a molecular switch, alternating between inactive GDP-bound and active GTP-bound states. Transition between these states is facilitated by guanine nucleotide exchange factors (GEFs) which load GTP and activate KRAS, and GTP hydrolysis, which is catalyzed by GTPase-activating proteins (GAPs) to inactivate KRAS. GTP-binding to KRAS promotes binding of effectors to trigger signal transduction pathways including RAF-MEK-ERK (MAPK). Somatic, activating mutations in KRAS are a hallmark of cancer and prevent the association of GAPs, thereby stabilizing effector-binding and enhancing KRAS signaling. Patients with KRAS mutant tumors have significantly poorer outcomes and worse prognosis. While there are clinically-approved inhibitors of several MAPK pathway proteins (e.g. MEK, BRAF, EGFR) for a subset of tumor types, to date there have been no clinical molecules that are selective for KRAS mutant tumors. Moreover, several MAPK-pathway targeted therapies are contra-indicated for treatment of KRAS mutant tumors due to lack of clinical efficacy. Additionally, non-tumor or non-mutant selective therapies can introduce on-target toxicities due to inhibition of MAPK signaling in normal cells. This might limit the utility for combining such agents with standard-of-care or immunotherapy. Thus, there exists a significant unmet need for the development of tumor-selective therapies that do not introduce liabilities for normal cells.

KRAS p.G12C is present in approximately 13% of lung adenocarcinoma, 3% of colorectal cancer, and 2% of other solid tumors. The mutant cysteine of $KRAS^{G12C}$ resides adjacent to a pocket (P2) present in the inactive GDP-bound form of KRAS. The proximity of P2 and a mutant cysteine led to a broad search for covalent inhibitors. The first reported electrophile screen of $KRAS^{G12C}$ led to the eventual identification of ARS-1620, which demonstrates in vivo efficacy in preclinical KRAS p.G12C models. While Araxes Pharma's ARS-1620 was a milestone for proof-of-concept, mutant-selective KRAS inhibition, it was positioned as a tool compound for preclinical studies. We identified a series of novel acrylamide-based molecules that utilize a previously unexploited surface groove in $KRAS^{G12C}$ to substantially enhance potency and selectivity. Intensive electrophile-screening and structure-based design culminated in the discovery of AMG 510, the first $KRAS^{G12C}$ inhibitor to reach clinical testing in humans (See www.clinicaltrials.gov NCT03600883). Here we present compelling clinical activity of AMG 510.

SUMMARY

Provided herein are methods of treating cancer comprising administering to a subject in need thereof Compound A in a daily dose of 180 mg, 360 mg, 720 mg, or 960 mg. In various cases, the daily dose is 180 mg. In various cases, the daily dose is 360 mg. In various cases, the daily dose is 720 mg. In various cases, the daily dose is 960 mg. The dose can be administered orally. The dose can be administered as a single daily dose. In various cases, the subject is administered Compound A for at least one months, or at least three months, or at least six months.

The subjects administered Compound in the methods disclosed herein have cancer. The cancer can be a solid tumor. The cancer can be a KRAS G12C mutated cancer. In some cases, the cancer is non-small cell lung cancer. In some cases, the cancer is colorectal cancer. In some cases, the cancer is pancreatic cancer. In various cases, the subject is one who, prior to start of therapy with Compound A, had undergone at least one (e.g., at least two) other systemic cancer therapy.

In various cases, a subject administered Compound A for at least a month does not exhibit any grade 3 or grade 4 adverse events associated with Compound A therapy. In some cases, the subject does not exhibit any grade 3 or grade 4 adverse events associated with Compound A therapy after at least three months of administration of Compound A. In various cases, the subject exhibits an at least stable disease after administration with Compound A. In some cases, the subject exhibits an at least partial response after administration with Compound A.

In various cases, the methods disclosed herein can further comprise administration of a chemotherapeutic. In some cases, the chemotherapeutic comprises an anti-PD1 antibody. In some cases, the anti-PD1 antibody is Pembrolizumab (Keytruda), Nivolumab, AUNP-12, AMG 404, or Pidilizumab. In some cases, the chemotherapeutic comprises an anti-PDL1 antibody. In some cases, the anti-PDL1 antibody is Atezolizumab, MPDL3280A, Avelumab or Durvalumab. In some cases, the chemotherapeutic comprises a MEK inhibitor. In some cases, the MEK inhibitor is trametinib, pimasertib, PD-325901, MEK162, TAK-733, GDC-0973 or AZD8330. In some cases, the chemotherapeutic comprises a CDK4/6 inhibitor. In some cases, the CDK4/6 inhibitor comprises abemaciclib, or palbociclib. In some cases, the chemotherapeutic comprises a PI3K inhibitor. In some cases, the PI3K inhibitor comprises AMG 511 or buparlisib.

BRIEF DESCRIPTION OF THE FIGURES

In the Figures that follow, PD indicates progressive disease, PR indicates partial response and SD indicates stable disease.

FIG. 12 shows the patients dosed with 180 mg daily of Compound A.

FIG. 13 shows the patients dosed with 360 mg daily of Compound A.

FIG. 14 shows the patients dosed with 720 mg daily of Compound A.

FIG. 15 shows the patients dosed with 960 mg daily of Compound A.

DETAILED DESCRIPTION

Figure 1:
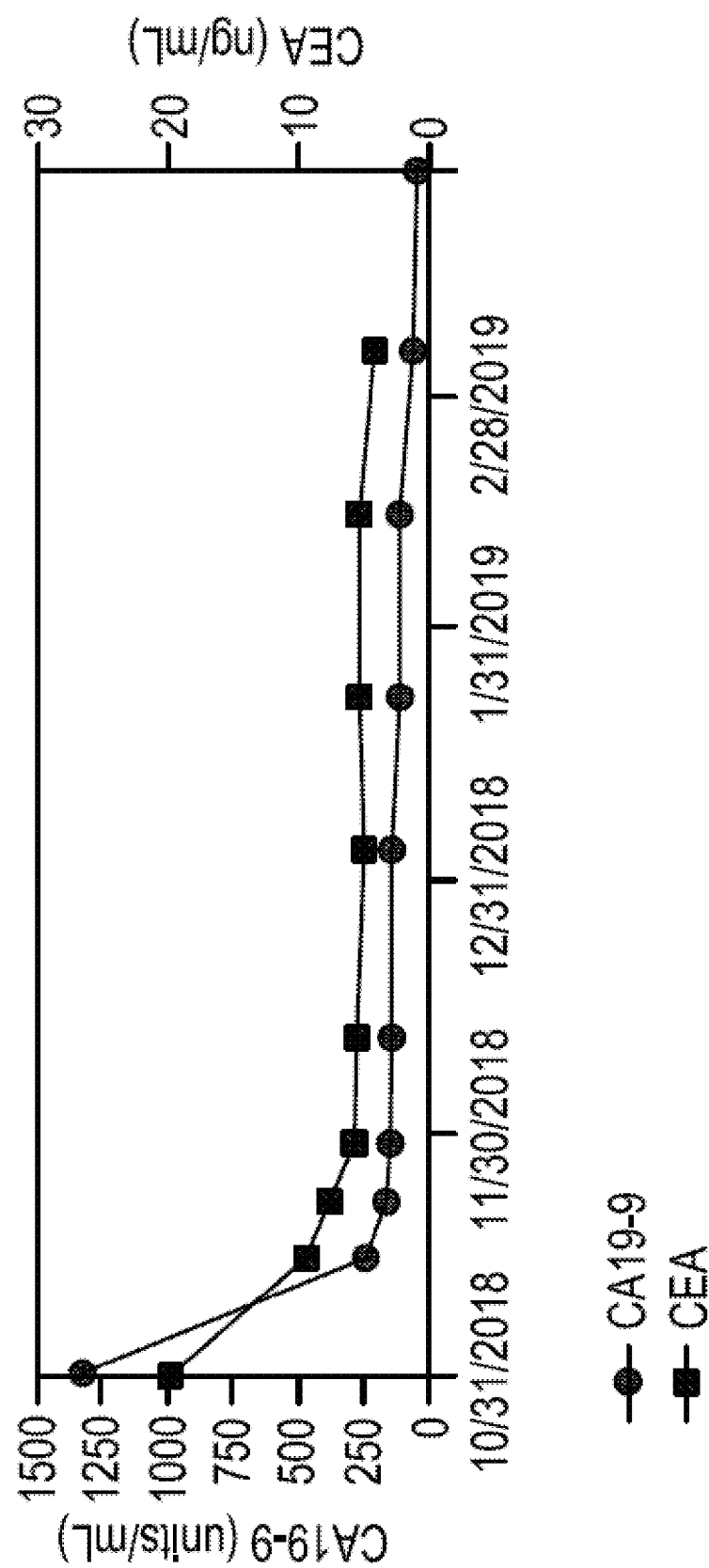
FIG. 1 shows CA 19-9 and CAE biomarker response in patient having metastatic colon adenocarcinoma and administered Compound A at a total daily dose of 360 mg.

Provided herein are methods of treating cancers by administering Compound A to a subject in need thereof. Compound A has a structure of

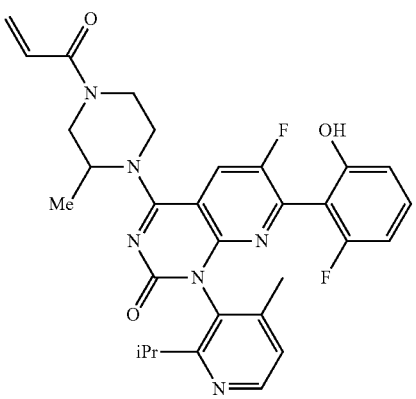

In some cases, Compound A is referred to as AMG 510. Compound A can be present as a pharmaceutically acceptable isotopically-labeled version, wherein one or more atoms is replaced by atoms having the same atomic number, but an atomic mass or mass number different from the atomic mass or mass number usually found in nature. Examples of isotopes that can be incorporated into Compound A include isotopes of hydrogen, carbon, nitrogen, oxygen, and fluorine, such as $^2H$, $^3H$, $^{11}C$, $^{13}C$, $^{14}C$, $^{13}N$, $^{15}N$, $^{15}O$, $^{17}O$, $^{18}O$, and $^{18}F$, respectively. These radiolabeled compounds could be useful to help determine or measure the effectiveness of Compound A, by characterizing, for example, the site or mode of action, or binding affinity to pharmacologically important site of action. Certain isotopically-labeled versions of Compound A, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of structure (I) can generally be prepared by conventional techniques known to those skilled in the art. Isotopically-labeled compounds as disclosed herein can generally be prepared by conventional techniques known to those skilled in the art.

Compound A may exist as a stereoisomer (i.e., isomers that differ only in the spatial arrangement of atoms) including optical isomers and conformational isomers (or conformers). Compound A, when referred to herein unless otherwise indicated, includes all stereoisomers, both as pure individual stereoisomer preparations and enriched preparations of each, and both the racemic mixtures of such stereoisomers as well as the individual diastereomers and enantiomers that may be separated according to methods that are known to those skilled in the art. In some cases, Compound A is provided as 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one:

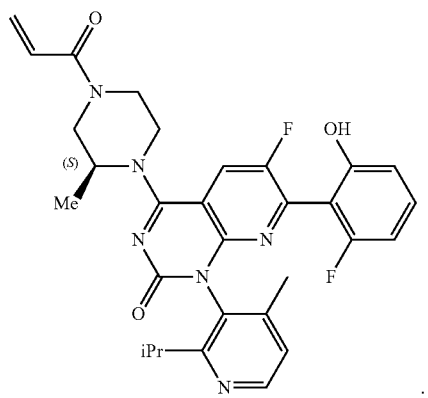

Compound A may exist as an atropisomer, which is a conformational stereoisomer that occurs when rotation about a single bond in the molecule is prevented, or greatly slowed, as a result of steric interactions with other parts of the molecule. Compound A, when referred to herein unless otherwise indicated, includes all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. The separation and isolation of the isomeric species is duly designated by the well known and accepted symbols "M" or "P". In some cases, Compound A is provided as 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one and the M-atropisomer:

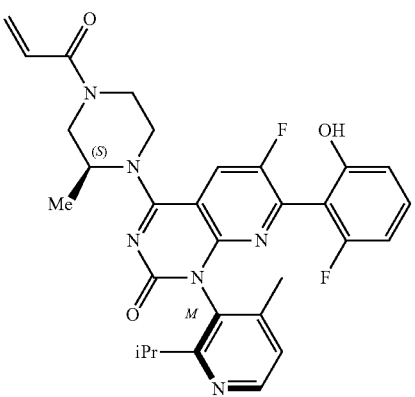

In some cases, Compound A is provided as 4-((R)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one and the M-atropisomer:

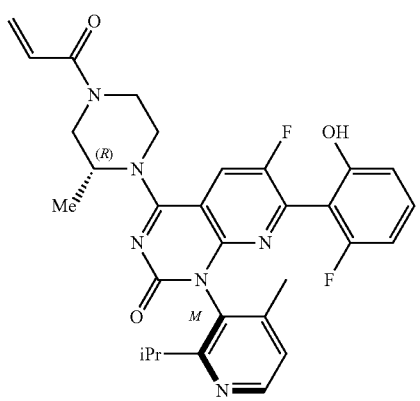

In some cases, Compound A is provided as 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one and the P-atropisomer:

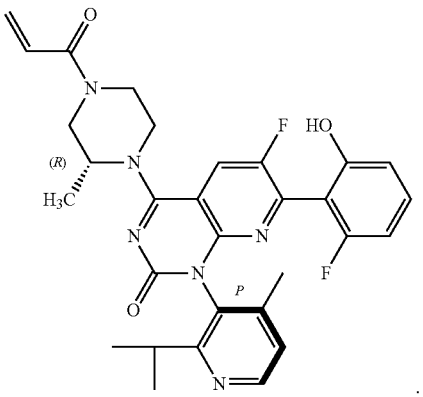

In some cases, Compound A is provided as 4-((R)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one and the P-atropisomer:

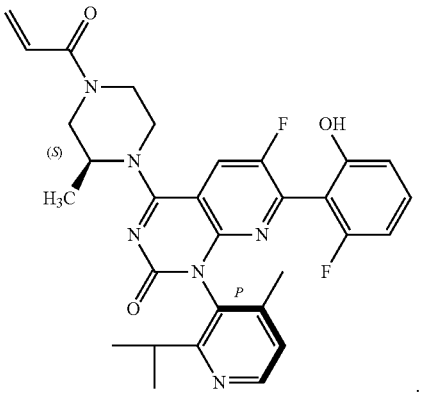

In some cases, Compound A is provided as mixtures of the above isomers.

Compound A can be prepared as reported previously, e.g., generally as disclosed in WO 2018/119183 or specifically as disclosed in WO 2018/217651.

Compound A can be provided as a pharmaceutically acceptable salt thereof. Contemplated examples of pharmaceutically acceptable salts include base addition salt and acid addition salts. Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine. Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Compound A can be combined with a pharmaceutically acceptable excipient to provide a pharmaceutical formulation (also referred to, interchangeably, as a composition). The excipient can be a diluent or carrier. Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials. The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

Pharmaceutical compositions containing Compound A can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining Compound A with pharmaceutically acceptable excipients such as carriers well known in the art. Such excipients and carriers enable Compound A to be formulated as tablets, pills, dragees, capsules, liquids, gels, syrups, slurries, suspensions and the like, for oral ingestion by a patient to be treated. Pharmaceutical preparations for oral use can be obtained by adding Compound A with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of Compound A is administered orally, the composition typically is in the form of a solid (e.g., tablet, capsule, pill, powder, or troche) or a liquid formulation (e.g., aqueous suspension, solution, elixir, or syrup). In one embodiment the therapeutically effective amount of Compound A (e.g., 960 mg) is administered orally in the form of a tablet or multiple tablets (e.g., 8×120 mg tablet).

When administered in tablet form, the composition can additionally contain a functional solid and/or solid carrier, such as a gelatin or an adjuvant. The tablet, capsule, and powder can contain about 1 to about 95% Compound A, and preferably from about 15 to about 90% Compound A.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight Compound A, and preferably about 1 to about 50% Compound A. In one embodiment contemplated, the liquid carrier is non-aqueous or substantially non-aqueous. For administration in liquid form, the composition may be supplied as a rapidly-dissolving solid formulation for dissolution or suspension immediately prior to administration.

When a therapeutically effective amount of Compound A is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to Compound A, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In some embodiments contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating Compound A in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of Compound A in contact with the body fluids in the GI tract, and to provide a substantially constant and effective level of the active compound in the blood plasma. For example, release can be controlled by one or more of dissolution, diffusion, and ion-exchange. In addition, the slow release approach may enhance absorption via saturable or limiting pathways within the GI tract. For example, the compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, Compound A is delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

Compound A can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of Compound A in water-soluble form. Additionally, suspensions can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of Compound A and allow for the preparation of highly concentrated solutions. Alternatively, a present composition can be in powder form for constitution with a suitable vehicle (e.g., sterile pyrogen-free water) before use.

Compound A also can be formulated in rectal compositions, such as suppositories or retention enemas (e.g., containing conventional suppository bases). In addition to the formulations described previously, Compound A can be formulated as a depot preparation. Such long-acting formulations can be administered by implantation (e.g., subcutaneously or intramuscularly) or by intramuscular injection. Thus, for example, Compound A can be formulated with suitable polymeric or hydrophobic materials (for example, as an emulsion in an acceptable oil) or ion exchange resins, or as sparingly soluble derivatives, for example, as a sparingly soluble salt.

In particular, Compound A can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound A also can be injected parenterally, for example, intravenously, intramuscularly, subcutaneously, or intracoronarily. For parenteral administration, the compound is best used in the form of a sterile aqueous solution which can contain other substances, for example, salts, or sugar alcohols, such as mannitol, or glucose, to make the solution isotonic with blood.

For veterinary use, Compound A is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using Compound A either alone or in combination with another agent or intervention traditionally used for the treatment of such disease may be packaged into a kit. Specifically, the present disclosure provides a kit for use in the therapeutic intervention of the disease comprising a packaged set of medicaments that include Compound A as well as buffers and other components for preparing deliverable forms of said medicaments, and/or devices for delivering such medicaments, and/or any agents that are used in combination therapy with Compound A, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of Compound A that results in achieving the desired effect. For example, a therapeutically effective amount of Compound A decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

While individual needs vary, determination of optimal ranges of effective amounts of the compound is within the skill of the art. For administration to a human in the curative or prophylactic treatment of the conditions and disorders identified herein, for example, typical dosages of the compounds of the present disclosure can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 1 mg/day to about 960 mg/day, about 20 mg/day to about 720 mg/day, about 3 mg/day to about 500 mg/day, about 5 mg/day to about 360 mg/day, about 10 mg/day to about 100 mg/day, about 3 mg/day to about 10 mg/day, about 100 mg/day to about 250 mg/day. Such doses may be administered in a single dose or it may be divided into multiple doses.

In specific embodiments, Compound A is administered to a subject in need thereof orally and once a day. In some cases, the subject is administered a total daily amount of 180 mg, 360 mg, 720 mg, or 960 mg. In some cases, the total daily amount of Compound A administered is 180 mg. In some cases, the total daily amount of Compound A administered is 360 mg. In some cases, the total daily amount of Compound A administered is 720 mg. In some cases, the total daily amount of Compound A administered is 960 mg. In some cases, Compound A is administered in a divided daily dose, such as two, three, four, five, or six times a day.

EMBODIMENTS

In a first embodiment, the present disclosure provides a method of treating cancer comprising administering to a subject in need thereof Compound A in a daily dose of 180 mg, 360 mg, 720 mg, or 960 mg, wherein Compound A has the following structure

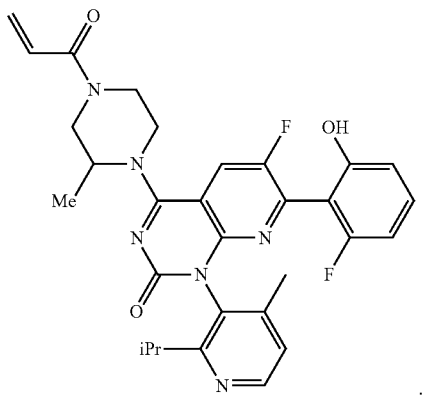 [SMILES: C=CC(=O)N1CCN(c2nc(=O)n(-c3c(C)ccnc3C(C)C)c3nc(-c4c(O)cccc4F)c(F)cc23)C(C)C1]

In a 2nd embodiment, the present disclosure provides the method of embodiment 1, wherein Compound A has the structure

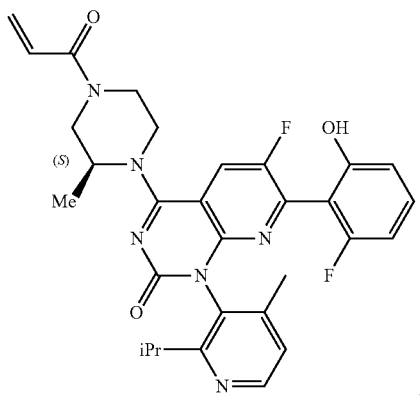

In a 3rd embodiment, the present disclosure provides the method of embodiment 1, wherein Compound A has the structure

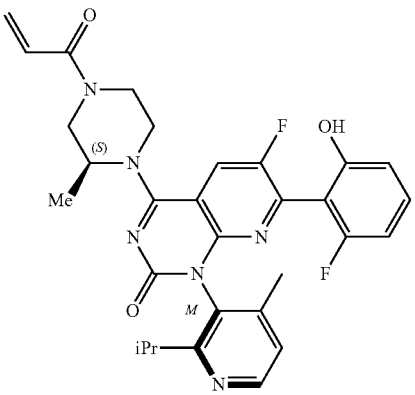

In a 4th embodiment, the present disclosure provides the method of any one of embodiments 1, 2 or 3, wherein the cancer is a solid tumor.

In a 5th embodiment, the present disclosure provides the method of any one of embodiments 1 2, 3 or 4, wherein the cancer is non-small cell lung cancer.

In a 6th embodiment, the present disclosure provides the method of any one of embodiments 1-4, wherein the cancer is colorectal cancer.

In a 7th embodiment, the present disclosure provides the method of any one of embodiments 1-4, wherein the cancer is pancreatic cancer.

In a 8th embodiment, the present disclosure provides the method of any one of embodiments 1 to 7, wherein the cancer is a KRAS G12C mutated cancer.

In a 9th embodiment, the present disclosure provides the method of any one of embodiments 1 to 8, wherein the subject, prior to start of Compound A therapy, had undergone at least one other systemic cancer therapy.

In a 10th embodiment, the present disclosure provides the method of embodiment 9, wherein the subject had undergone at least two other systemic cancer therapies.

In a 11th embodiment, the present disclosure provides the method of any one of embodiments 1 to 9, wherein Compound A is administered orally.

In a 12th embodiment, the present disclosure provides the method of any one of embodiments 1 to 11, wherein the Compound A is administered as a single daily dose.

In a 13th embodiment, the present disclosure provides the method of any one of embodiments 1 to 12, wherein the subject does not exhibit any grade 3 or grade 4 adverse events associated with Compound A therapy after administration of Compound A for at least 1 month.

In a 14th embodiment, the present disclosure provides the method of embodiment 13, wherein the subject does not exhibit any grade 3 or grade 4 adverse events associated with Compound A therapy after administration of Compound A for at least 3 months.

In a 15th embodiment, the present disclosure provides the method of any one of embodiments 1 to 14, wherein the Compound A dose is 180 mg.

In a 16th embodiment, the present disclosure provides the method of any one of embodiments 1 to 14, wherein the Compound A dose is 360 mg.

In a 17th embodiment, the present disclosure provides the method of any one of embodiments 1 to 14, wherein the Compound A dose is 720 mg.

In a 18th embodiment, the present disclosure provides the method of any one of embodiments 1 to 14, wherein the Compound A dose is 960 mg.

In a 19th embodiment, the present disclosure provides the method of any one of embodiments 1 to 18, wherein the subject is administered Compound A for at least one month.

In a 20th embodiment, the present disclosure provides the method of any one of embodiments 1 to 18, wherein the subject is administered Compound A for at least three months.

In a 21st embodiment, the present disclosure provides the method of any one of embodiments 1 to 18, wherein the subject is administered Compound A for at least six months.

In a 22nd embodiment, the present disclosure provides the method of any one of embodiments 19 to 21, wherein the subject exhibits at least a stable disease (SD).

In a 23rd embodiment, the present disclosure provides the method of embodiment 22, wherein the subject exhibits at least a partial response (PR).

In a 24th embodiment, the present disclosure provides the method of any one of embodiments 1 to 23, wherein the subject does not exhibit a dose limiting toxicity (DLT).

In a 25th embodiment, the present disclosure provides the method of any one of embodiments 1 to 24, wherein Compound A is as the M atropisomer.

In a 26th embodiment, the present disclosure provides the method of any one of embodiments 1 to 25, further comprising administering to the subject a chemotherapeutic.

In a 27th embodiment, the present disclosure provides the method of embodiment 24, wherein the chemotherapeutic comprises an anti-PD1 antibody.

In a 28th embodiment, the present disclosure provides the method of embodiment 25, wherein the anti-PD1 antibody is Pembrolizumab (Keytruda), Nivolumab, AUNP-12, AMG 404, or Pidilizumab.

In a 29th embodiment, the present disclosure provides the method of embodiment 26, wherein the chemotherapeutic comprises an anti-PDL1 antibody.

In a 30th embodiment, the present disclosure provides the method of embodiment 29, wherein the anti-PDL1 antibody is Atezolizumab, MPDL3280A, Avelumab or Durvalumab.

In a 31st embodiment, the present disclosure provides the method of embodiment 26, wherein the chemotherapeutic comprises a MEK inhibitor.

In a 32nd embodiment, the present disclosure provides the method of embodiment 31, wherein the MEK inhibitor is trametinib, pimasertib, PD-325901, MEK162, TAK-733, GDC-0973 or AZD8330.

In a 33rd embodiment, the present disclosure provides the method of embodiment 26, wherein the chemotherapeutic comprises a CDK4/6 inhibitor.

In a 34th embodiment, the present disclosure provides the method of embodiment 33, wherein the CDK4/6 inhibitor comprises abemaciclib, or palbociclib.

In a 35th embodiment, the present disclosure provides the method of embodiment 26, wherein the chemotherapeutic comprises a PI3K inhibitor.

In a 36th embodiment, the present disclosure provides the method of embodiment 35, wherein the PI3K inhibitor comprises AMG 511 or buparlisib.

In a 37th embodiment, the present disclosure provides the method of embodiment 22, wherein the stable disease is neither sufficient shrinkage to qualify for PR nor sufficient increase to qualify for PD.

In a 38th embodiment, the present disclosure provides the method of embodiment 23, wherein the partial response is at least a 30% decrease in the sum of diameters of target lesions.

In an alternative first embodiment, the present disclosure provides Compound A in a daily dose of 180 mg, 360 mg, 720 mg, or 960 mg, for use in treating cancer, wherein Compound A has the following structure

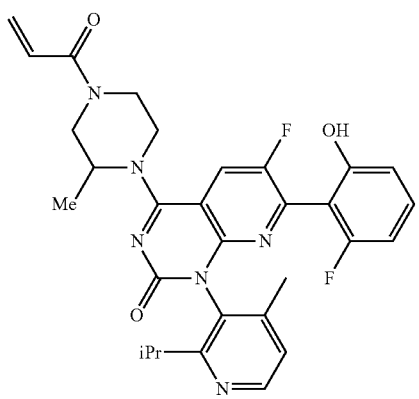

In another alternative first embodiment, the present disclosure provides a use of Compound A in a daily dose of 180 mg, 360 mg, 720 mg, or 960 mg in the preparation of a medicament for treating cancer, wherein Compound A has the following structure

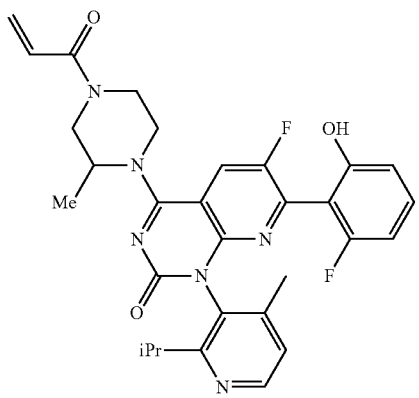

Methods of Using Compound A

In embodiments of the methods disclosed herein, the subject is administered Compound A at a disclosed dose for at least one month, at least six weeks, at least two months, at least three months, at least four months, at least five months, or at least six months.

In some embodiments of the methods disclosed herein, the subject is administered Compound A at a disclosed dose orally at least once daily (QD).

In some embodiments of the methods disclosed herein, the subject is administered Compound A at a disclosed dose orally at least twice daily (BID).

The present disclosure provides a method of inhibiting RAS-mediated cell signaling comprising contacting a cell with an effective amount of Compound A. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in $k_{off}$ of GTP or a decrease in $k_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using Compound A or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of Compound A as disclosed herein to a subject in need thereof. In some embodiments, the cancer is mediated by a KRAS, HRAS or NRAS G12C mutation. In various embodiments, the cancer is pancreatic cancer, colorectal cancer or lung cancer (e.g., non-small cell lung cancer (locally advanced or metastatic)). In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of Compound A or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount Compound A.

KRAS, HRAS or NRAS G12C mutations have also been identified in hematological malignancies (e.g., cancers that affect blood, bone marrow and/or lymph nodes). Accordingly, certain embodiments are directed to administration of Compound A (e.g., in the form of a pharmaceutical composition) to a patient in need of treatment of a hematological malignancy. Such malignancies include, but are not limited to leukemias and lymphomas. For example, Compound A can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CIVIL), Acute monocytic leukemia (AMoL) and/or other leukemias. In other embodiments, Compound A is useful for treatment of lymphomas such as all subtypes of Hodgkins lymphoma or non-Hodgkins lymphoma. In various embodiments, Compound A is useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of Compound A, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CIVIL), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In some embodiments, the methods for treatment are directed to treating lung cancers, the methods comprise administering an effective amount of Compound A (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of Compound A. Modulation can be inhibiting or activating protein activity. In some embodiments, the disclosure provides methods of inhibiting protein activity by contacting the G12C Mutant KRAS, HRAS or NRAS protein with an effective amount of Compound A in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of Compound A. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, BRAS or NRAS G12C activity in a cell by contacting said cell with an amount of Compound A sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of Compound A sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of Compound A sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of Compound A sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of Compound A sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of Compound A sufficient to inhibit the activity of KRAS, HRAS or NRAS G12C in said human. The present disclosure provides methods of treating a disease mediated by KRAS, HRAS or NRAS G12C activity in a subject in need of such treatment.

Subject Selection and Therapeutic Results

In some embodiments, the subject being treated by Compound A in the disclosed methods is one who has undergone at least one or more prior systemic cancer therapies (e.g., Compound A is a second or third line therapy). In some embodiments, the subject being treated by Compound A in the disclosed methods is one who has disease progression following at least one prior systemic cancer therapy (i.e., Compound A is a second line therapy). In some embodiments, the subject being treated by Compound A in the disclosed methods is one who has disease progression following at least two prior systemic cancer therapies (i.e., Compound A is a third line therapy). Prior systemic cancer therapies can be any therapy approved by a regulatory authority (e.g., the FDA or EMA) as treatment given type and stage of cancer. In some cases, the prior systemic cancer therapy is a cancer therapy not yet approved by a regulatory authority but undergoing clinical trials. If a subject has had a prior systemic cancer therapy, in some cases, the subject has not undergone any systemic cancer therapy for at least one month, at least two months. at least three months, at least four months, at least five months, or at least six months prior to starting therapy as disclosed herein with Compound A.

In some embodiments, the subject will exhibit pathologically documented, locally-advanced or metastatic malignancy with KRAS p. G12C mutation identified through molecular testing. The mutation will be confirmed by central testing prior to enrollment.

In some embodiments, for NSCLC, subjects may have received platinum-based combination therapy and/or targeted therapies (i.e., if molecular testing has identified mutations in EGFR, ALK, or proto-oncogene tyrosine-protein kinase ROS [ROS1] or expression of programmed death-ligand [PD-L1]), prior to receiving AMG 510 (Compound A).

In some embodiments, the NSCLC in subjects must have progressed after receiving anti-PD1 or anti-PD-L1 immunotherapy (unless contraindicated) and/or platinum-based combination chemotherapy and targeted therapy (if actionable oncogenic driver mutations were identified [i.e., EGFR, ALK, and ROS1]). Subjects must have received no more than 3 prior lines of therapy.

In some embodiments for colorectal cancer (CRC), subjects must have received at least 2 prior systemic regimens in the metastatic setting. For those CRC subjects with tumors that are MSI-H, at least 1 of the prior systemic regimens must be treatment with either nivolumab or pembrolizumab if they were clinically able to receive inhibitors and 1 of these agents is approved for that indication in the region or country.

In some embodiments, the CRC in subjects must have progressed after receiving fluoropyrimidine and oxaliplatin and irinotecan. For those CRC subjects with tumors that are MSI-H, at least 1 of the prior systemic regimens must have included an anti-PD1 therapy if they were clinically able to receive inhibitors and 1 of these agents is approved for that indication in the region or country.

In some embodiments, for advanced solid tumor types other than NSCLC or CRC, subjects must have received at least one prior systemic therapy of be intolerant or ineligible for available therapies known to provide clinical benefit.

In some embodiments, dosages of Compound A may optionally be administered to a subject with food, such as consuming a standardized high-fat, high calorie meal, or in a fasting state (no food or liquids, except for water for ≥10 hours). In one embodiment, the dose of Compound A (e.g., 960 mg once daily) is administered with or without food.

A subject undergoing a therapy is monitored for adverse events (AE) during the course of the therapy. A treatment related AE is an AE that is related to the treatment drug. A treatment emergent AE is one that a subject develops undergoing the treatment that was not present prior to start of therapy. In some cases, the treatment emergent AE is not or suspected not to be related to the treatment itself AEs are characterized as one of five grades—grade 1 is a mild AE; grade 2 is a moderate AE; grade 3 is a severe AE; grade 4 is a life-threatening or disabling AE; and grade 5 is death related to AE. In some cases, the subject does not exhibit any grade 3 AE that is treatment related. In some cases, the subject does not exhibit any grade 3 AE. In some cases, the subject does not exhibit any grade 4 AE that is treatment related. In some cases, the subject does not exhibit any grade 4 AE. In various cases, the subject does not exhibit a grade 3 or grade 4 AE that is treatment related after administration of Compound A for at least one month, or at least three months.

In various cases, the subject being treated with Compound A in the methods disclosed herein, does not exhibit any dose limiting toxicities (DLT) at the dose administered. A DLT is any AE meeting the criteria listed below occurring during the first treatment cycle of Compound A (day 1 through day 21) where relationship to the drug cannot be ruled out. The grading of AEs is based on the guidelines provided in the CTCAE version 5.0. AEs for DLT assessment: Hematological toxicity: Febrile neutropenia; Neutropenic infection; Grade 4 neutropenia; Grade ≥3 thrombocytopenia for >7 days; Grade 3 thrombocytopenia with grade ≥2 bleeding; Grade 4 thrombocytopenia; Grade 4 Anemia Non-hematological toxicity Grade ≥4, vomiting or diarrhea; Grade 3 diarrhea or grade 3 vomiting lasting more than 3 days despite optimal medical support; Grade ≥3 nausea for 3 days or more despite optimal medical support; Any other grade ≥3 AE In various cases, the subject of the disclosed methods exhibits a response to the therapy. In some cases, the subject exhibits at least a stable disease (SD) due to administration of Compound A. In some cases, the subject exhibits at least a partial response (PR) due to administration of Compound A. The response of a subject is assessed by the criteria as defined by RECIST 1.1, e.g., as discussed in Eisenhauer et al., *Eur J Cancer*, 45:228-247 (2009). A complete response (CR) is disappearance of all target lesions and any pathological lymph nodes have a reduction in short axis to less than 10 mm. A partial response (PR) is at least a 30% decrease in the sum of diameters of target lesions, taking as reference the baseline sum diameters. A progressive disease is at least a 20% increase in the sum of diameters of target lesions, taking as reference the smallest sum on study (including the baseline sum if that is the smallest on study), and there must be an absolute increase of at least 5 mm in addition to the relative increase of 20%. A stable disease is neither sufficient shrinkage to qualify for PR nor sufficient increase to qualify for PD. A controlled disease state is when a patient may alternate between exhibiting a stable disease and a partial response. The tumor size can be measured by radiographic scan.

Combination Therapy

The present disclosure also provides methods for combination therapies in which an agent known to modulate other pathways, or other components of the same pathway, or even overlapping sets of target enzymes are used in combination with Compound A, or a pharmaceutically acceptable salt thereof. In one aspect, such therapy includes but is not limited to the combination of Compound A as disclosed herein with a chemotherapeutic agent to provide a synergistic or additive therapeutic effect.

Many chemotherapeutics are presently known in the art and can be used in combination with Compound A. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), Venclexta™ (venetoclax) and Adriamycin™, (docorubicin) as well as a host of chemotherapeutic agents. Non-limiting examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, chlorocyclophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Compound A can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Compound A is contemplated for use in co-therapies with a chemotherapeutic that is an anti-neoplastic agent, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Compound A can be used in combination with a chemotherapeutic that is an PD1 inhibitor, PDL1 inhibitor, MEK inhibitor, PI3K inhibitor, or CDK4/6 inhibitor.

The KRAS$^{G12C}$ inhibitors of the present disclosure can be used in combination with MEK inhibitors. Particular MEK inhibitors that can be used in the combinations of the present disclosure include PD-325901, trametinib, pimasertib, MEK162 [also known as binimetinib], TAK-733, GDC-0973 and AZD8330. A particular MEK inhibitor that can be used along with KRAS$^{G12C}$ inhibitor in the combinations of the present disclosure is trametinib (tardename: Mekinist®, commercially available from Novartis Pharmaceuticals Corp.). Another particular MEK inhibitor is N-(((2R)-2,3-dihydroxypropyl)oxy)-3,4-difluoro-2-((2-fluoro-4-iodophenyl)amino)benzamide, also known as AMG 1009089, 1009089 or PD-325901. Another particular MEK inhibitor that can be used in the combinations of the present disclosure includes cobimetinib. In some cases, the MEK inhibitor is CI-1040, AZD6244, PD318088, PD98059, PD334581, RDEA119, ARRY-142886, ARRY-438162, or PD-325901.

In another aspect, Compound A can be used in combination with one or more agents that is an inhibitor of a protein in the phosphatidylinositol 3-kinase (PI3K) pathway. Examples of proteins in the PI3K pathway include PI3K, mTOR and PKB (also known as Akt or AKT). The PI3K protein exists in several isoforms including α, β, δ, or γ. It is contemplated that a PI3K inhibitor can be selective for one or more isoform. By selective it is meant that the compounds inhibit one or more isoform more than other isoforms. Selectivity is a concept well known to those is the art and can be measured with well-known in vitro or cell-based activity assays. Preferred selectivity includes greater than 2-fold, preferably 10-fold, or more preferably 100-fold greater selectivity for one or more isoform over the other isoforms. In one aspect, the PI3K inhibitors that can be used in combination with Compound A are PI3K α selective inhibitors. In another aspect the compound is a PI3K δ selective inhibitor. In still another aspect, the compound is a PI3K β selective inhibitor.

Examples of PI3K inhibitors that can be used in combination with Compound A include those disclosed in the following: PCT published application no. WO2010/151791; PCT published application no. WO2010/151737; PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581;U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

In particular, PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

Preferred PI3K inhibitors for use in combination with the compound of the present disclosure include:

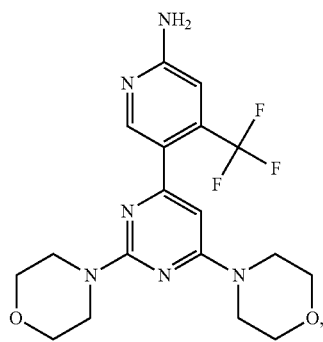 [SMILES: Nc1cc(C(F)(F)F)c(-c2cc(N3CCOCC3)nc(N3CCOCC3)n2)cn1]

also known as buparlisib, an investigational small molecule from Novartis Pharmaceuticals,

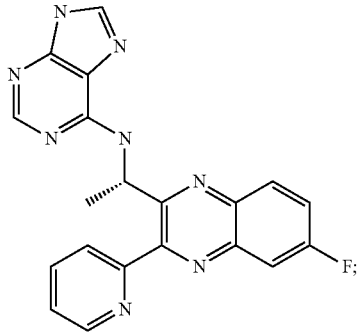

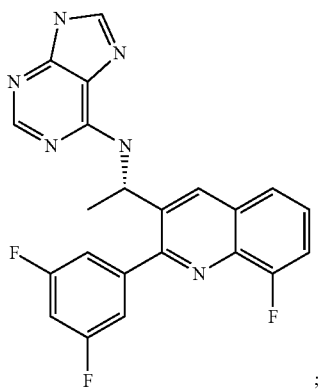

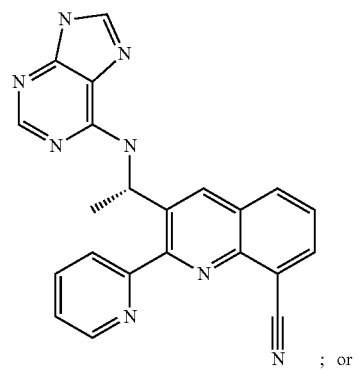

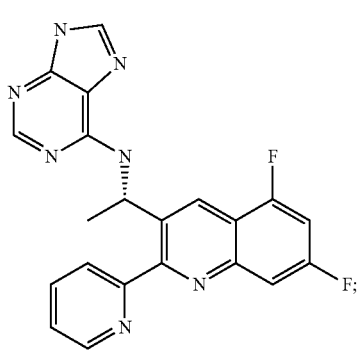

or a pharmaceutically acceptable salt thereof.

Also preferred is as a PI3K inhibitor is a compound of Formula IIa below, or a pharmaceutically acceptable salt thereof,

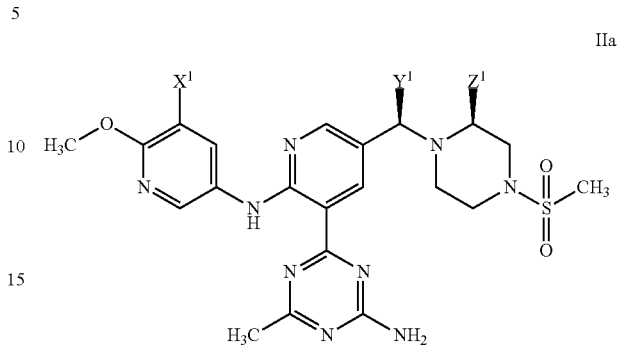

IIa wherein $X^1$ is fluorine or hydrogen; $Y^1$ is hydrogen or methyl; and $Z^1$ is hydrogen or methyl. A particular PI3K inhibitor that can be used in the combinations is AMG 511 (also known as AMG 2539965 or 2539965), which is Example 148 of published PCT application WO2010/126895.

Other PI3K inhibitors that can be used in combination with Compound A in the combinations disclosed herein include Pan-PI3K inhibitors such as BKM120 and GDC-0941; PI3Kα selective inhibitors such as AMG 511 and BYL719; and PI3K β selective inhibitors such as GSK-2636771.

Compounds that inhibit both PI3K and mTOR (dual inhibitors) are known. In still another aspect, the present disclosure provides the use of dual PI3K and mTOR inhibitors for use in combination with $KRAS^{G12C}$ inhibitors. An example of a particular dual inhibitor is GDC-0980.

mTOR is a protein in the PI3K pathway. It is another aspect of the present disclosure to use an mTOR inhibitor in combination with $KRAS^{G12C}$ inhibitors. mTOR inhibitors that can be used in combination with Compound A include those disclosed in the following documents: PCT published application no. WO2010/132598 and PCT published application no. WO2010/096314. mTOR inhibitors that can be used in combination with Compound A include AZD2014 and MLN0128.

PKB (AKT) is also a protein in the PI3K pathway. It is another aspect to use an AKT inhibitor in combination with Compound A. AKT inhibitors that can be used include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897,619; or PCT published application no. WO 2010/083246 A1. Particular AKT inhibitors that can be used in the combinations include MK-2206, GDC-0068 and AZD5363.

Compound A can also be used in combination with CDK4 and/or 6 inhibitors. CDK 4 and/or 6 inhibitors that can be used in the present combinations include, but are not limited to, those disclosed in the following documents: PCT published application no. WO 2009/085185 or U.S. patent application publication no. US2011/0097305.

Anti-PD-1 antibodies include, but are not limited to, Pembrolizumab (Keytruda™) Nivolumab, AUNP-12, AMG401, and Pidilizumab. Exemplary anti-PD-1 antibodies and methods for their use are described by Goldberg et al., *Blood* 110(1):186-192 (2007), Thompson et al., *Clin. Cancer Res.* 13(6):1757-1761 (2007), and Korman et al., International Application No. PCT/JP2006/309606 (publication no. WO 2006/121168 A1), each of which are expressly incorporated by reference herein.

Compound A can be used in combination with the agents disclosed herein or other suitable agents, depending on the condition being treated. Hence, in some embodiments Compound A will be co-administered with other agents as described above. When used in combination therapy, Compound A is administered with the second agent simultaneously or separately. This administration in combination can include simultaneous administration of the two agents in the same dosage form, simultaneous administration in separate dosage forms, and separate administration. That is, Compound A and any of the agents described above can be formulated together in the same dosage form and administered simultaneously. Alternatively, Compound A and any of the agents described above can be simultaneously administered, wherein both the agents are present in separate formulations. In another alternative, Compound A can be administered just followed by and any of the agents described above, or vice versa. In some embodiments of the separate administration protocol, Compound A and any of the agents described above are administered a few minutes apart, or a few hours apart, or a few days apart.

EXAMPLES

Phase 1 Study of Compound A

A. First Results

Compound A Dosing Study: patients identified with a cancer having a KRAS G12C mutation were enrolled in the study. The patients are adult patients with locally advanced or metastatic KRAS G12 C mutant solid tumors. All patients previously received prior standard therapies depending upon the tumor type and stage of disease. No patient exhibited active brain metastases. Patients in the dosing study had the following diagnoses: 14 with non-small cell lung cancer (NSCLC), 10 with colorectal cancer (CRC) and two with another KRAS G12 C mutant solid tumor. Compound A was administered orally once daily at the designated dose. Patients were given a dose of 180 mg, 360 mg, 720 mg, or 960 mg Compound A and adiographic scans were performed every six weeks.

Adverse events reported while taking Compound A are shown in Tables 1 and 2 below. Of the six serious adverse events reported, none was reported as related to Compound A. The six serious adverse events were two Grade 3 (1 Pneumonia, 1 Malignant biliary obstruction); one Grade 4 (Pericardial effusion); and three Fatal (1 Dyspnea; 2 Colorectal cancer metastatic). No patient reported any DLTs, Grade 4 related adverse events, or serious related adverse events.

TABLE 1

Treatment Emergent Adverse Event

| Adverse Event | Gr 1 n | Gr 2 n | Gr 3 n | All Grades n |
|---|---|---|---|---|
| Any Treatment Emergent Adverse Event | | | | 25 |
| Decreased Appetite | 3 | 3 | 0 | 6 |
| Diarrhoea | 5 | 0 | 1 | 6 |
| Fatigue | 1 | 3 | 1 | 5 |

TABLE 1-continued

Treatment Emergent Adverse Event

| Adverse Event | Gr 1 n | Gr 2 n | Gr 3 n | All Grades n |
|---|---|---|---|---|
| Headache | 3 | 1 | 1 | 5 |
| Cough | 2 | 2 | 0 | 4 |
| Hot Flush | 4 | 0 | 0 | 4 |
| Nausea | 4 | 0 | 0 | 4 |

TABLE 2

Treatment Related Adverse Event

| Adverse Event | Gr 1 n | Gr 2 n |
|---|---|---|
| Diarrhoea | 3 | |
| Decreased appette | 2 | |
| Nausea | 2 | |
| Elevated creatine phosphokinase | 1 | |
| Elevated or change in AST | 1 | 1 |
| Elevated or change in ALT | 1 | 1 |
| Alkaline phosphatase | 1 | 1 |
| Cheilitis | | 1 |
| Dry mouth | 1 | |
| Flatulence | 1 | |
| Vomiting | 1 | |
| Fatigue | 1 | |
| Hyperkalemia | | 1 |
| WBC Decrease | 1 | |
| Proteinuria | | 1 |
| Pyrexia | 1 | |
| Arthralgia | 1 | |
| Hot Flush | 1 | |

| Grade 3 Adverse Event | n |
|---|---|
| Anemia | 1 |
| Diarrhea | 1 |

[a]Patient had grade 2 anemia at baseline;
[b]Lasting 2 days

Individual response to Compound A therapy: Case #1: A 61 year old woman diagnosed with KRAS G12C metastatic NSCLC in 2010, had prior therapy of Carboplatin/Taxol from August 2010 until October 2010; then Carboplatin/Pemetrexed from October 2016 until June 2017; then Nivolumab from August 2017 until April 2018; then was administered Compound A at a 180 mg dose. She exhibited a partial response at the 180 mg dose (−34%) at one of her six-week assessments. She has tolerated the drug and continues on it for more than 27 weeks.

Case #2: A 59 year old man diagnosed with a KRAS G12 C metastatic NSCLC in 2013, had prior therapy of Carboplatin/Pemetrexed February 2014 until February 2015; Erlotinib from April 2015 until June 2015; Nivolumab August 2015 until August 2017; Dasatinib from July 2016 until August 2017; M3541 (Targeted biologics) from October 2017 until November 2017; then was administered Compound A at a 360 mg dose. He exhibited a partial response (−80%) at one of his six-week assessments. He has tolerated the drug and continues on it for more than 14 weeks.

Case #3: A 34 year old woman diagnosed with KRAS G12C metastatic colon adenocarcinoma in 2014, had prior therapy of FOLFOX and HIPEC in Aug 2015, followed by FOLOX till December 2015; FOLFIRI with PD in August 2016; HIPEC Oct 2016; Capecitabine+bevacizumab August 2017; Phase I clinical trial March-June 2018; then was enrolled in October 2018 Phase I clinical trial for Compound A and administered Compound A at a dose of 360 mg. She exhibited a stable disease (−18%) at one of her six-week assessments. She also exhibited a biochemical response where her biomarkers CA 19-9 and CAE decreased rapidly upon administration of Compound A, and remained at the lower levels during the course of the Compound A therapy (FIG. 1). She has tolerated the drug and continues on treatment for more than 22 weeks.

Figure 2:
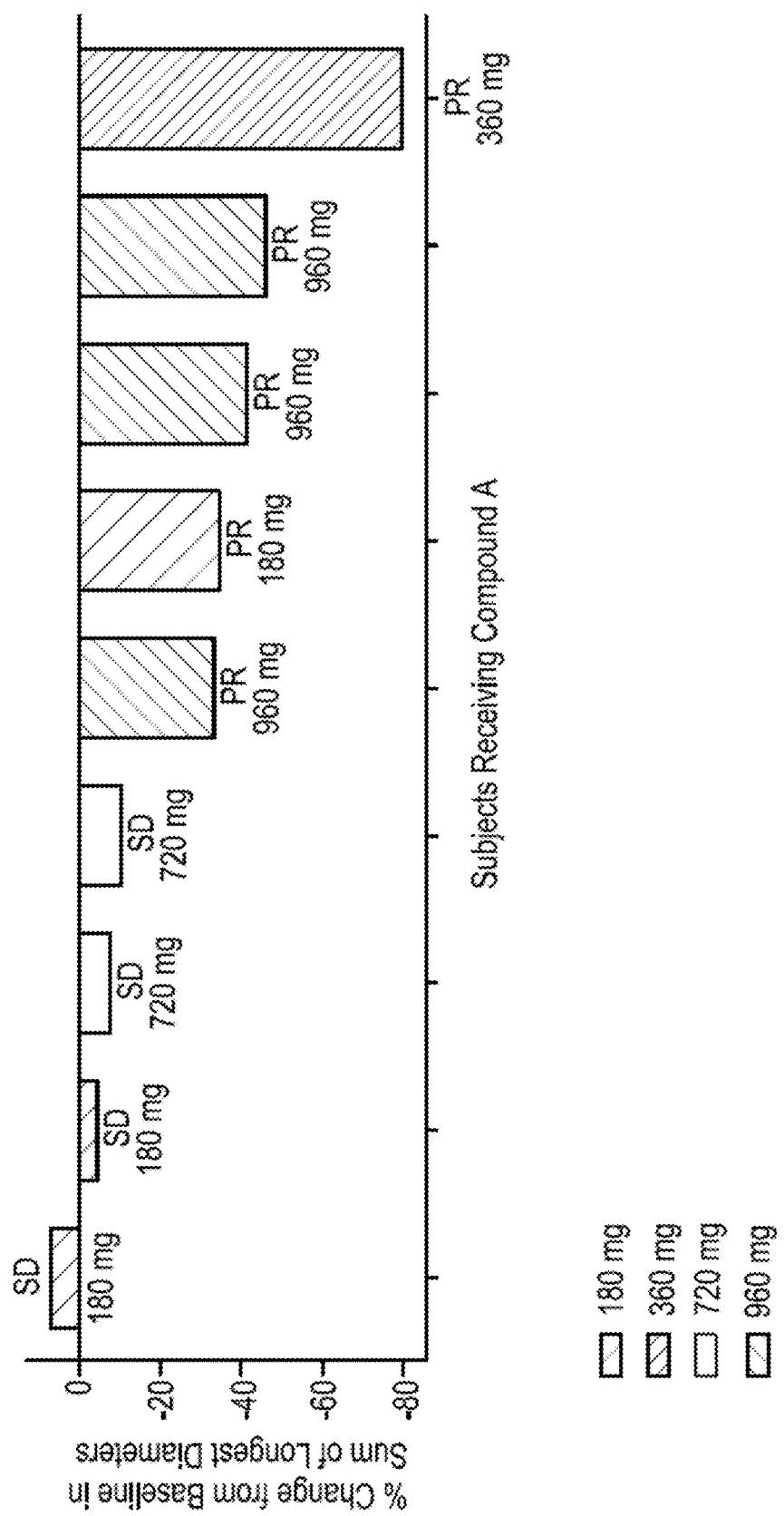
FIG. 2 shows non-small cell lung cancer (NSCLC) tumor responses, as measured by radiographic scans every six weeks, for nine NSCLC cancer patients receiving Compound A at various total daily doses as shown.
Figure 3:
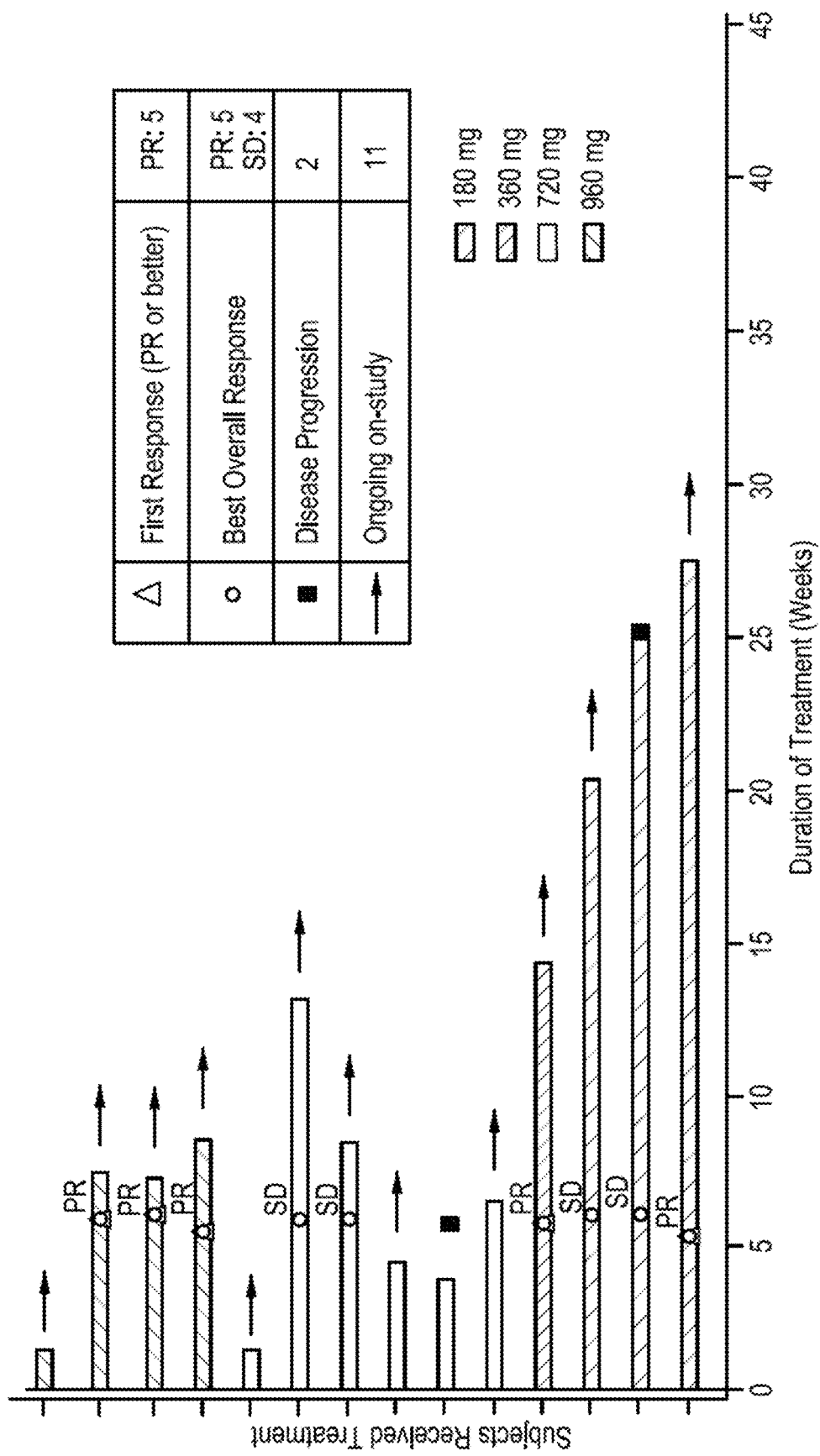
FIG. 3 shows the response and treatment duration of NSCLC patients administered Compound A at the following total daily doses—top four bars 960 mg; next six bars 720 mg; next bar 360 mg; and bottom three bars 180 mg.

NSCLC Tumor Responses: Patients having KRAS G12C NSCLC were given a daily dose of 180 mg, 360 mg, 720 mg, or 960 mg, and 9 of the 10 patients studied exhibited at least a stable disease response to the therapy based upon radiographic scans performed every six weeks—results shown in FIG. 2 with designated dose noted below each histogram. Duration and treatment of the subjects in the NSCLC study are also shown in FIG. 3, where top four bars are for patients receiving a 960 mg total daily dose, next six bars are for patients receiving 720 mg total daily dose; next bar for patient receiving a 360 mg total daily dose, and bottom three bars for patients receiving a 180 mg total daily dose.

Figure 4:
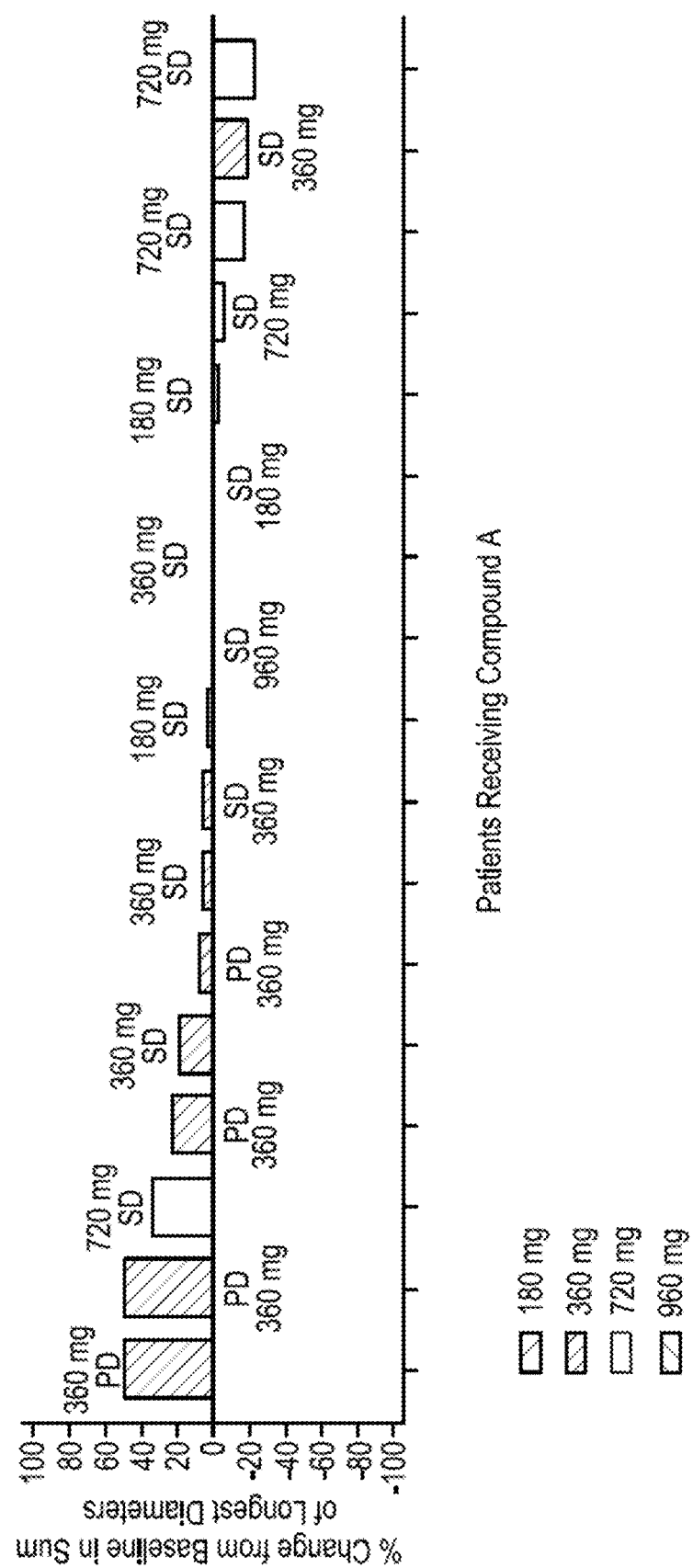
FIG. 4 shows colorectal cancer (CRC) and other solid tumor responses, as measured by radiographic scans every six weeks, for CRC and other solid tumor cancer patients receiving Compound A at various total daily doses as shown.
Figure 5:
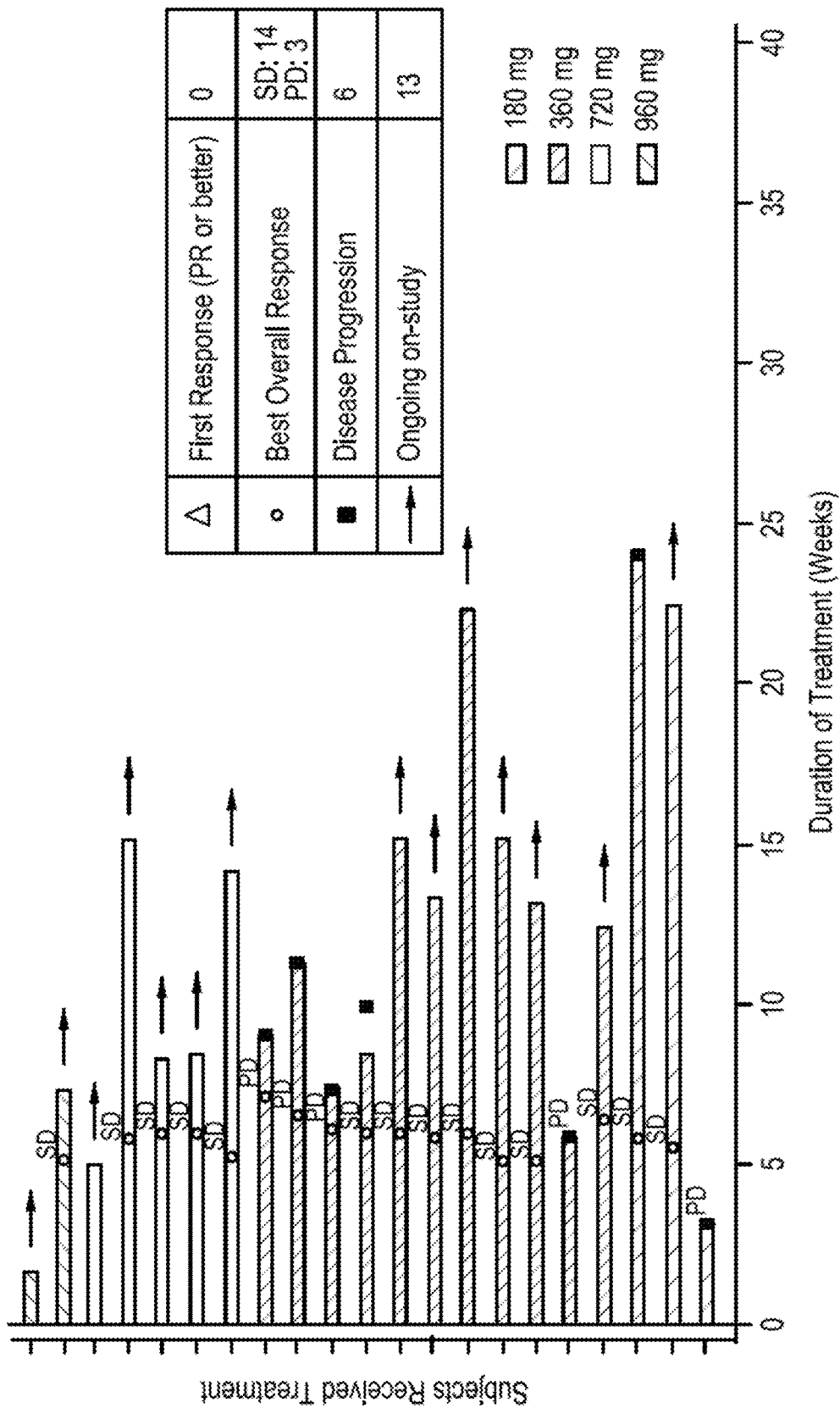
FIG. 5 shows the response and treatment duration of CRC and Other solid tumor patients administered Compound A at the following total daily doses—top two bars 960 mg; next five bars 720 mg; next eleven bars 360 mg; and bottom three bars 180 mg.

CRC and Other Solid Tumor Responses: Patients having a KRAS G12C CRC or other solid tumor were given a daily dose of 180 mg, 360 mg, 720 mg, or 960 mg, and results for 17 of the 19 patients studied are shown in FIG. 4 (the two not shown progressed prior to week 6 and were not subject to the first six-week assessment). The results in FIG. 4 are based upon radiographic scans performed at each six-week assessment. Duration and treatment of the subjects in the CRC/Other study are also shown in FIG. 5, where top two bars are for patients receiving a 960 mg total daily dose, next five bars are for patients receiving 720 mg total daily dose; next eleven bars for patients receiving a 360 mg total daily dose, and bottom three bars for patients receiving a 180 mg total daily dose.

Compound A Phase 1 Study Results: thirty five patients having a KRAS G12C cancer (19 CRC, 14 NSCLC, 2 other—appendix) were enrolled in the phase 1 study for Compound A. All had 2 or more prior lines of therapy. No DLTs were reported. Sixteen patients reported Compound A—related adverse events, two with Grade 3 related adverse events (anemia and diarrhea). The best tumor responses were tabulated, and 26 patients remain on the study. Results are shown below in the Table 3.

TABLE 3

Treatment Related Adverse Event
Best Tumor Response in 29* Patients

|  | Frequency | Duration of Response or Stable Disease** |
|---|---|---|
| NSCLC (n = 10) |  |  |
| Partial Response | 5 (2 confirmed) | 7.3-27.4 weeks |
| Stable Disease | 4 | 8.4-25.1 weeks |
| Progressive Disease | 1*** | n/a |
| CRC/Other (n = 19) |  |  |
| Stable Disease | 14 | 7.3-24.0 weeks |
| Progressive Disease | 5*** | n/a |

*Six pts (4 NSCLC; 2 CRC/Other) did not have a post-baseline radiographic scan as of the data cutoff date (4 Apr. 2019).
**Duration of response as of the data cutoff date. All 5 pts with partial response are still on treatment as of the data cutoff date.
***Two of these pts (1 NSCLC; 1 CRC) had early (prior to week 6) clinical progressive disease.

The pharmacokinetics of a Compound A 960 mg orally administered dose is as follows: $C_{max}$ of 7.84 µg mL (SD of 8.09); $AUC_{0-24hr}$ 140 hr*µg/mL (SD of 117); and $t_{1/2,z}$ 6.5 hr (SD of 4.2-8.0).

B. Updated Results

Updated results of this study have been presented as a poster by Govindan, R., et. al., "Phase 1 Study of AMG 510, a Novel KRAS$^{G12C}$ Inhibitor, in Advanced Solid Tumors With KRAS p. G12C Mutation," at the meeting of the European Society of Medical Onclology (ESMO), Sep. 27-Oct. 1, 2019, in Barcelona, Spain, the content of which is herewith incorporated in its entirety. Further results of this study will be presented by Fakih, M. G., et al., "CodeBreak 100: activity of AMG 510, a novel small molecule inhibitor of KRAS$^{G12C}$, in patients with advanced colorectal cancer," and Hong, D. S., et al., "CodeBreak 100: Phase 1 study of AMG 510, a novel KRAS$^{G12C}$ inhibitor, in patients with advanced solid tumors other than non-small-cell lung cancer (NSCLC) and colorectal cancer (CRC)," at the American Society of Clinical Oncology (ASCO) Meeting, May 29-31, 2020 (virtual), the contents of which are herewith incorporated in their entireties.

The study is also published as "A Phase 1/2, Study Evaluating the Safety, Tolerability, PK, and Efficacy of AMG 510 in subjects with a Specific KRAS Mutation (CodeBreak 100)," Clinicaltrials.gov Identifier No. NCT03600883, https://clinicaltrials.gov/ct2/show/NCT03600883 (last accessed May 3, 2020), the contents of which are herewith incorporated in their entirety.

The following data shows that Compound A demonstrated early promising antitumor activity in patients with advanced solid tumors harboring a KRAS p. G12C mutation, such as NSCLC, CRC and other tumor types.

The clinical trial design is briefly described in the scheme below.

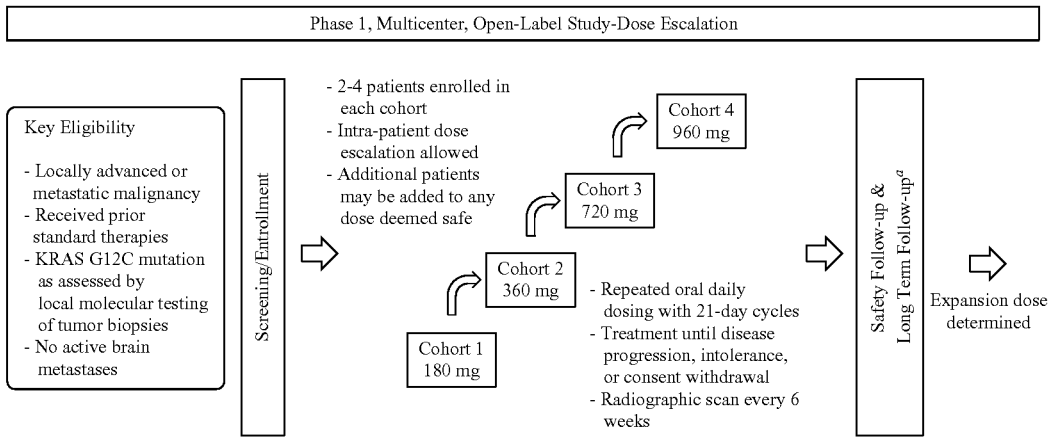

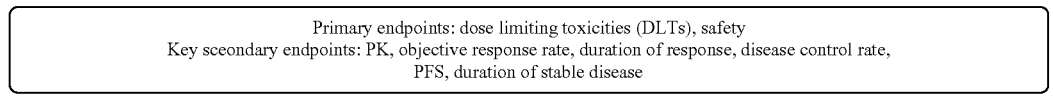

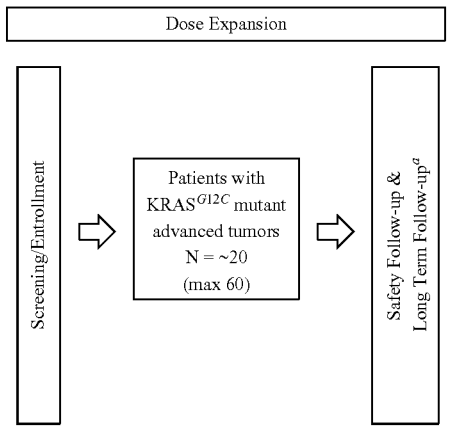

[a] 30 (+7) days after end of treatment for safety follow-up; every 12 weeks for long term follow-up. PK: pharmacokinetics; PFS: progression-free survival.

I. Patients With Non-Small-Cell Lung Cancer (NSCLC)

The first patient was enrolled on Aug. 27, 2018. By the cutoff date of Jul. 17, 2019, 76 patients were enrolled, of those 34 with NSCLC (one with SCLC (this patient was recorded as SCLC ("other tumor type" category) as of the data cutoff and changed to NSCLC by the participating site after cutoff). 45 patients enrolled in the escalation cohort (180 mg total daily dose (N=6), 360 mg total daily dose (N=13), 720 mg total daily dose (N=11), 960 mg total daily dose (N=15)) and 31 patients enrolled in the expansion cohort (960 mg total daily dose (N=31)), resulting in 55 evaluable patients, who had the first 6-week scan or early progressive disease (PD). Of the 76 enrolled patients, 52 remained on treatment and 24 discontinued treatment due to PD (N=22) and death (N=2). Of note here is that none of the discontinuations was caused by treatment-related adverse effects.

TABLE 4

Baseline Characteristics

| Baseline Characteristics | N = 76 |
|---|---|
| Median age (range) - year | 59.0 (33.0-78.0) |
| Female - n (%) | 40 (52.6) |
| Primary Tumor Type - n (%) | |
| NSCLC | 34 (44.7) |
| CRC | 36 (47.4) |
| SCLC[a] | 1 (1.3) |
| Appendiceal cancer | 3 (3.9) |
| Endometrial cancer | 1 (1.3) |
| Small bowel cancer | 1 (1.3) |
| ECOG performance status at baseline - n (%) | |
| 0 | 20 (26.3) |
| 1 | 53 (69.7) |
| 2 | 3 (3.9) |

TABLE 4-continued

Baseline Characteristics

| Baseline Characteristics | N = 76 |
|---|---|
| Prior lines of systematic anticancer therapy - n (%) | |
| 1 | 5 (6.6) |
| 2 | 9 (11.8) |
| >2 | 62 (81.6) |
| Number of prior systemic anticancer therapies - median (range) | 4.0 (1-10) |

[a] The tumor type of this patient was recorded as SCLC (other tumor types) by the data cutoff; the participating site updated the tumor type to NSCLC after cutoff.
CRC = colorectal cancer;
ECOG = Eastern Cooperative Oncology Group;
NSCLC = non-small cell lung cancer;
SCLC = small cell lung cancer.

The following table summarizes the patient incidence of adverse events (AEs). No dose-limiting toxicities were reported. Further, no treatment-related serious or fatal AEs were reported. Most importantly, no treatment-related AEs lead to treatment discontinuation. As a result, 960 mg total daily dose of Compound A was identified as the expansion dose and recommended Phase 2 dose.

TABLE 5

Summary of Patient Incidence of Adverse Events (AEs)

| | All AEs (N = 76) – n (%) | All treatment-related AEs (N = 76) – n (%) |
|---|---|---|
| Any grade | 57 (75.0) | 26 (34.2) |
| Grade ≥2 | 44 (57.9) | 14 (18.4) |
| Grade ≥3 | 24 (31.6) | 6 (7.9) |
| Grade ≥4 | 8 (10.5) | 0 (0) |
| Dose-limiting toxicity | 0 (0) | 0 (0) |
| Serious ABs | 17 (22.4) | 0 (0)[c] |
| Fatal ABs | 7 (9.2)[a] | 0 (0) |
| ABs leading to treatment discontinuation | 2 (2.6)[b] | 0 (0) |

[a] Seven patients had the following fatal AEs: dyspnea, aspiration, lung cancer metastatic, colorectal cancer metastatic, and spinal compression fracture; none was related to treatment.
[b] Two patients with CRC discontinued treatment due to AE of colorectal cancer metastatic.
[c] One NSCLC patient had respiratory infection, which was initially reported as a treatment-related serious AE in the snapshot; after snapshot, the study site confirmed that it was not attributed to treatment but the underlying disease.
CRC = colorectal cancer;
NSCLC = non-small cell lung cancer.

The patient incidence of treatment-related adverse events (AEs) is shown in detail in the table below. In summary, 26 of 76 patients (34.2%) reported treatment-related AEs, most of which were grade 1 or 2. 6 of 76 patients (7.9%) reported 1 or more grade 3 treatment-related adverse events (diarrhea and anemia). There were no grade 4 or higher treatment-related adverse events.

TABLE 6

Patient Incidence of Treatment-Related Adverse Events (AEs)

| | Any Grade (N = 76) n (%) | Grade 3 (N = 76) n (%) |
|---|---|---|
| Any treatment-related AE | 26 (34.2) | 6 (7.9) |
| Diarrhea | 11 (14.5) | 4 (5.3) |
| Nausea | 3 (3.9) | 0 (0) |
| Dry mounth | 2 (2.6) | 0 (0) |
| Abominal pain | 1 (1.3) | 0 (0) |
| Cheilitis | 1 (1.3) | 0 (0) |
| Eructation | 1 (1.3) | 0 (0) |
| Flatulence | 1 (1.3) | 0 (0) |

TABLE 6-continued

Patient Incidence of Treatment-Related Adverse Events (AEs)

| | Any Grade (N = 76) n (%) | Grade 3 (N = 76) n (%) |
|---|---|---|
| Vomiting | 1 (1.3) | 0 (0) |
| ALT increased | 2 (2.6) | 0 (0) |
| AST increased | 2 (2.6) | 0 (0) |
| Blood alkaline phosphate increased | 2 (2.6) | 0 (0) |
| Blood creatine phosphokinase increased | 2 (2.6) | 0 (0) |
| Alanine aminotransferase | 1 (1.3) | 0 (0) |
| Aspartate aminotransferase | 1 (1.3) | 0 (0) |
| Lymphocyte count decreased | 1 (1.3) | 0 (0) |
| White blood cell count decreased | 1 (1.3) | 0 (0) |
| Anemia | 3 (3.9) | 3 (3.9) |
| Leukopenia | 1 (1.3) | 0 (0) |
| Decreased appetite | 2 (2.6) | 0 (0) |
| Hyperkalemia | 1 (1.3) | 0 (0) |
| Hypokalemia | 1 (1.3) | 0 (0) |
| Fatigue | 2 (2.6) | 0 (0) |
| Dysgeusia | 1 (1.3) | 0 (0) |
| Neuropathy peripheral | 1 (1.3) | 0 (0) |
| Arthralgia | 1 (1.3) | 0 (0) |
| Proteinuria | 1 (1.3) | 0 (0) |
| Epistaxis | 1 (1.3) | 0 (0) |
| Rash | 1 (1.3) | 0 (0) |
| Hot flush | 1 (1.3) | 0 (0) |

ALT = alanine aminotransferase;
AST = asnartate aminotransferase.

The pharmacokinetic (PK) profile of Compound A (960 mg oral total daily dose) as of the PK cutoff date of Jul. 24, 2019 (N=32, including patients with NSCLC and CRC) is as follows (geometric mean; % coefficient of variation (CV)): maximum serum concentration ($C_{max}$) 7.50 µg/mL (98.3%), area under the curve (AUC) 65.3 hr*µg/mL (81.7%), and elimination half life ($t_{1/2,z}$) 5.5 hr (1.8). The serum concentration after administration remains for at least 22 hr above the 90% inhibitory concentration in vitro ($IC_{90}$) in a 2 hr cellular phosphorylated extracellular signal-regulated kinase (pERK) assay.

The best tumor response of patients with NSCLC with all dose levels and with the 960 mg dose is reported in the table below.

TABLE 7

Patient Incidence of Treatment-Related Adverse Events (AEs)

| Efficacy outcomes | Evaluable patients (N = 23) | Evaluable patients receiving 960 mg (N = 13) |
|---|---|---|
| Best overall response | | |
| PR - n (%) | 11 (48) | 7 (54) |
| SD - n (%) | 11 (48) | 6 (46) |
| PD - n (%) | 1 (4) | 0 (0) |
| Objective response rate[a] | 48% | 54% |
| Disease control rate[b] | 96% | 100% |

[a] Evaluation of response is based on modified RECIST 1.1 criteria.
[b] PR or SD at week 6.
PR: partial response;
SD: stable disease;
PD: progressive disease.
Evaluable patients: patients who had the first 6-week scan or early PD.

Figure 6:
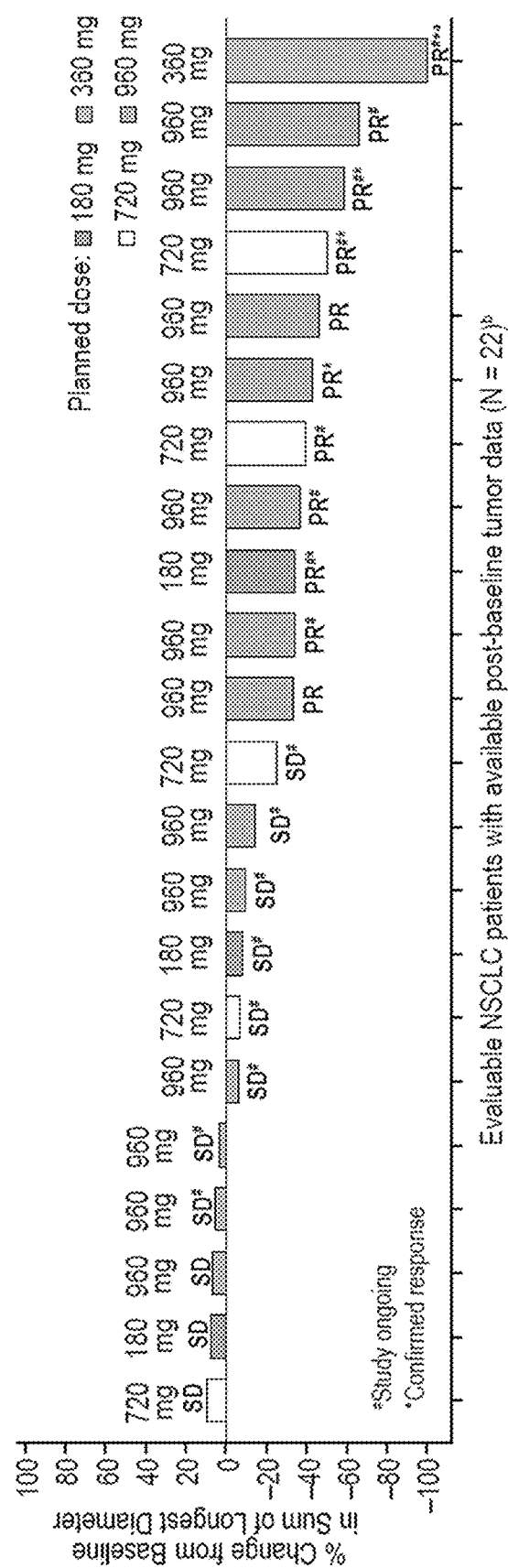
FIG. 6 shows the efficacy of Compound A in NSCLC patients as change in tumor burden from baseline. The superscript "a" on the far right bar indicates that the patient had complete response to the target lesion. The superscript "b" indicates that 1 patient discontinued study due to clinical PD prior to the 1st assessment without available post-baseline tumor burden data, and therefore is not shown on the graph.

The efficacy of Compound A in patients with NSCLC is shown in FIG. 6 (% change from baseline in sum of longest diameter v. evaluable NSCLC patients with available post-baseline tumor data (N=22). Of note, the patient represented by the bar on the far right, treated with a total daily dose of 960 mg had a complete response to the target lesion.

Figure 7:
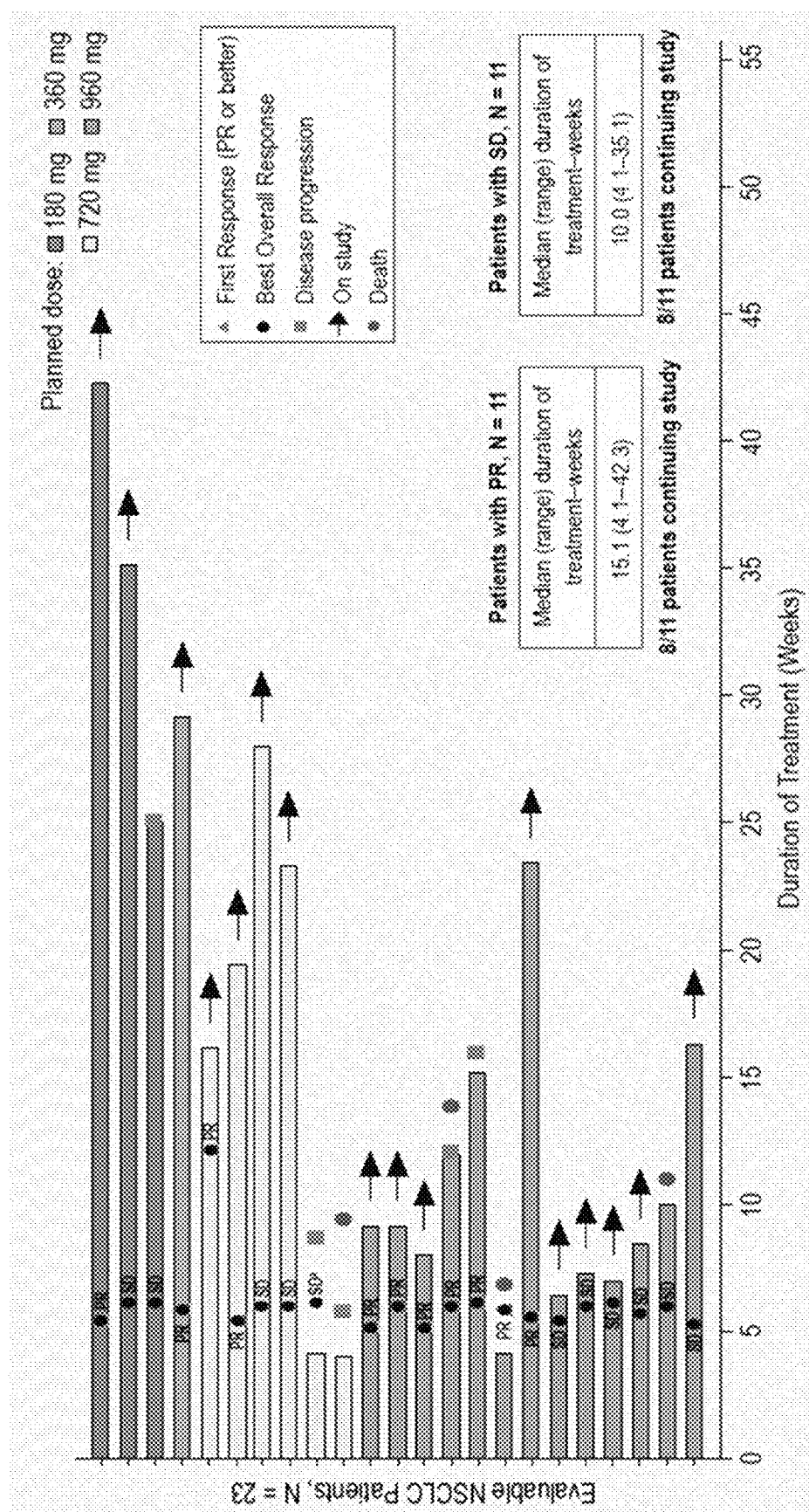
FIG. 7 shows the efficacy of Compound A in NSCLC patients in time to response and duration of treatment. Each bar in the graph, 23 in total, represents a certain patient (N=23), who was administered a particular total daily dose (counting from the top of the graph, bars 1-3 (180 mg), bar 4 (360 mg), bars 5-10 (720 mg), and bars 11-23 (960 mg). The superscript "a" on bar 9 indicates that the graph was plotted based on the data received from the participating sites as of the data cutoff. Duration of treatment data for this patient (bar 9) might be missing from the study site.

FIG. 7 shows the efficacy of Compound A in patients with NSCLC looking at time to response and duration of treatment (evaluable NSCLC patients (N=23) v. the duration of treatment in weeks). 11 patients showed a partial response (PR) with median duration of 15.1 treatment weeks (range 4.1-42.3). 8 of these 11 patients are continuing with the study. Further, 11 patients showed stable disease (SD) with a median duration of 10.0 treatment weeks (range 4.1-35.1). 8 of these 11 patients are continuing with the study.

In conclusion, Compound A demonstrated early promising antitumor activity in patients with advanced solid tumors harboring a KRAS p. G12C mutation, such as NSCLC. Additionally, Compound A has been found to have a favorable safety profile at the dose levels tested—no dose-limiting toxicities have been observed and no cumulative toxicities were noted with extended treatment.

II. Patients With Colorectal Cancer (CRC)

By the cutoff date of Jan. 8, 2020, 42 patients with CRC were enrolled (Cohort 1: 3 patients at 180 mg total daily dose, Cohort 2: 10 patients at 360 mg total daily dose, Cohort 3: 4 patients at 720 mg total daily dose; Cohort 4: 25 patients at 960 mg total daily dose). The median follow-up period was 7.9 months (range: 4.2-15.9 months). 8 patients were continuing treatment. 34 patients discontinued due to disease progression (32) and requests from patients (2). All enrolled patients had received prior lines of systemic anti-cancer therapy. 45% of patients received more than 3 lines of treatment.

TABLE 8

Baseline Characteristics

| Baseline Characteristics | N = 42 |
| --- | --- |
| Median age (range) - year | 57.5 (33-82) |
| Female - n (%) | 21 (50) |
| ECOG performance status at baseline - n (%) | |
| 0 | 17 (40.5) |
| 1 | 25 (59.5) |
| Prior lines of systematic anticancer therapy - n (%) | |
| 1 | 2 (4.8) |
| 2 | 11 (26.2) |
| 3 | 10 (23.8) |
| >3 | 19 (45.2) |
| Number of prior systemic anticancer therapies - median (range) | 3 (1-4) |

ECOG = Eastern Cooperative Oncology Group

The following two tables summarize the patient incidence of adverse events (AEs). 20 of 42 patients reported treatment-related adverse events, most of which were grade 2 or lower. Diarrhea and anemia were reported as grade 3 treatment-related AEs, occurring in 1 patient each. There were no dose-limiting toxicities. As discussed above, the 960 mg total daily dose of Compound A was identified as the expansion dose and recommended Phase 2 dose.

TABLE 9

Summary of Patient Incidence of Adverse Events (AEs)

| | Treatment-Emergent AEs (TEAEs), N = 42, n (%) | Treatment-related TEAEs N = 42, n (%) |
| --- | --- | --- |
| Any grade | 38 (90.5) | 20 (47.6) |
| Grade ≥2 | 29 (69.0) | 9 (21.4) |
| Grade ≥3 | 13 (31.0) | 2 (4.8) |
| Grade ≥4 | 3 (7.1) | 0 (0.0) |
| Dose-limiting toxicities | 0 (0.0) | 0 (0.0) |
| Serious AEs | 10 (23.8) | 0 (0.0) |
| Fatal AEs | 3 (7.1) | 0 (0.0) |
| AEs leading to treatment discountinuation | 2 (4.8) | 0 (0.0) |

AE: adverse event

TABLE 10

Treatment-Related TEAEs of any Grade Occurring in >1 Patients

| Treatment-related TEAEs of any grade occurring in >1 patients | N = 42, n (%) |
| --- | --- |
| Diarrhea | 8 (19.0) |
| Fatigue | 4 (9.5) |
| Nausea | 2 (4.8) |
| Blood creatine phosphokinase increase | 2 (4.8) |
| Anemia | 2 (4.8) |
| Vomiting | 2 (4.8) |

The tumor response of patients with CRC with all dose levels and with the 960 mg total daily dose is reported in the table below. As for efficacy, a confirmed partial response was observed in 3 patients, all of whom received the 960 mg dose. Responses were durable and still ongoing as of the data cutoff In addition, 29 patients had stable disease, resulting in a disease control rate of 76.2%.

TABLE 11

Tumor Response

| Tumor response | All dose levels N = 42, n (%) | 960 mg total daily dose N = 25, n (%) |
| --- | --- | --- |
| Best overall response | | |
| Confirmed partial response - n (%) | 3 (7.1) | 3 (12.0) |
| Stable disease - n (%) | 29 (69.0) | 17 (68.0) |
| Progressive disease - n (%) | 9 (21.4) | 4 (16.0) |
| Not done - n (%)$^a$ | 1 (2.4) | 1 (4.0) |
| Objective response rate - % | 7.1 | 12.0 |
| (95% CI) | (1.50, 19.48) | (2.55, 31.22) |
| Disease control rate - % | 76.2 | 80.0 |
| (95% CI) | (60.55, 87.95) | (59.30, 93.17) |
| Duration of response for 3 responders - months | 1.4+, 4.2+, 4.3+ | 1.4+, 4.2+, 4.3+ |
| Duration of stable disease - months Median (min, max) | 4.2 (2.5+, 11.0) | 4.2 (2.6, 5.7+) |

$^a$Patient had clinical progression and no postbaseline measurement.
+: censored value.

Figure 8:
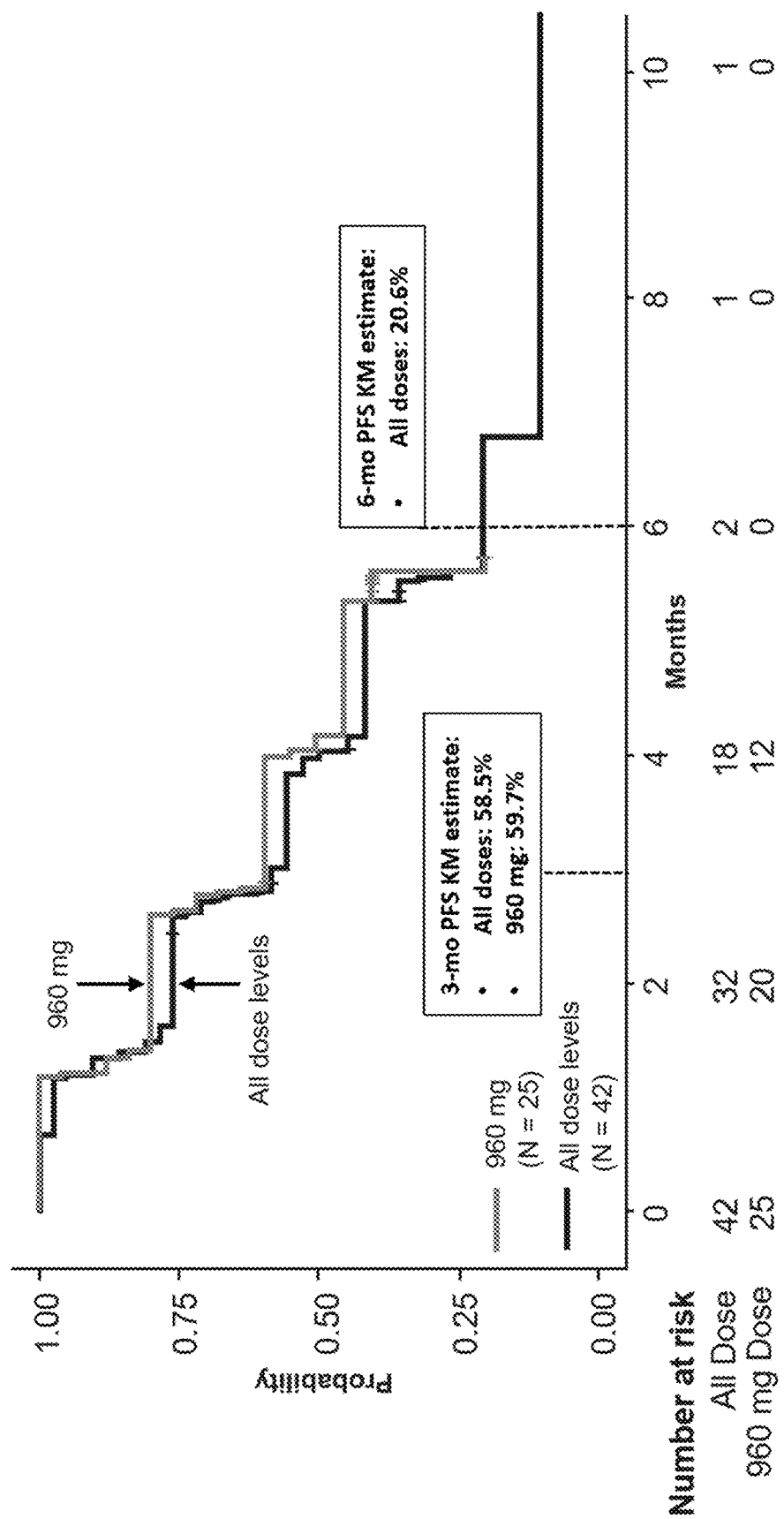
FIG. 8 shows the progression free survival probability of patients with CRC.
Figure 9:
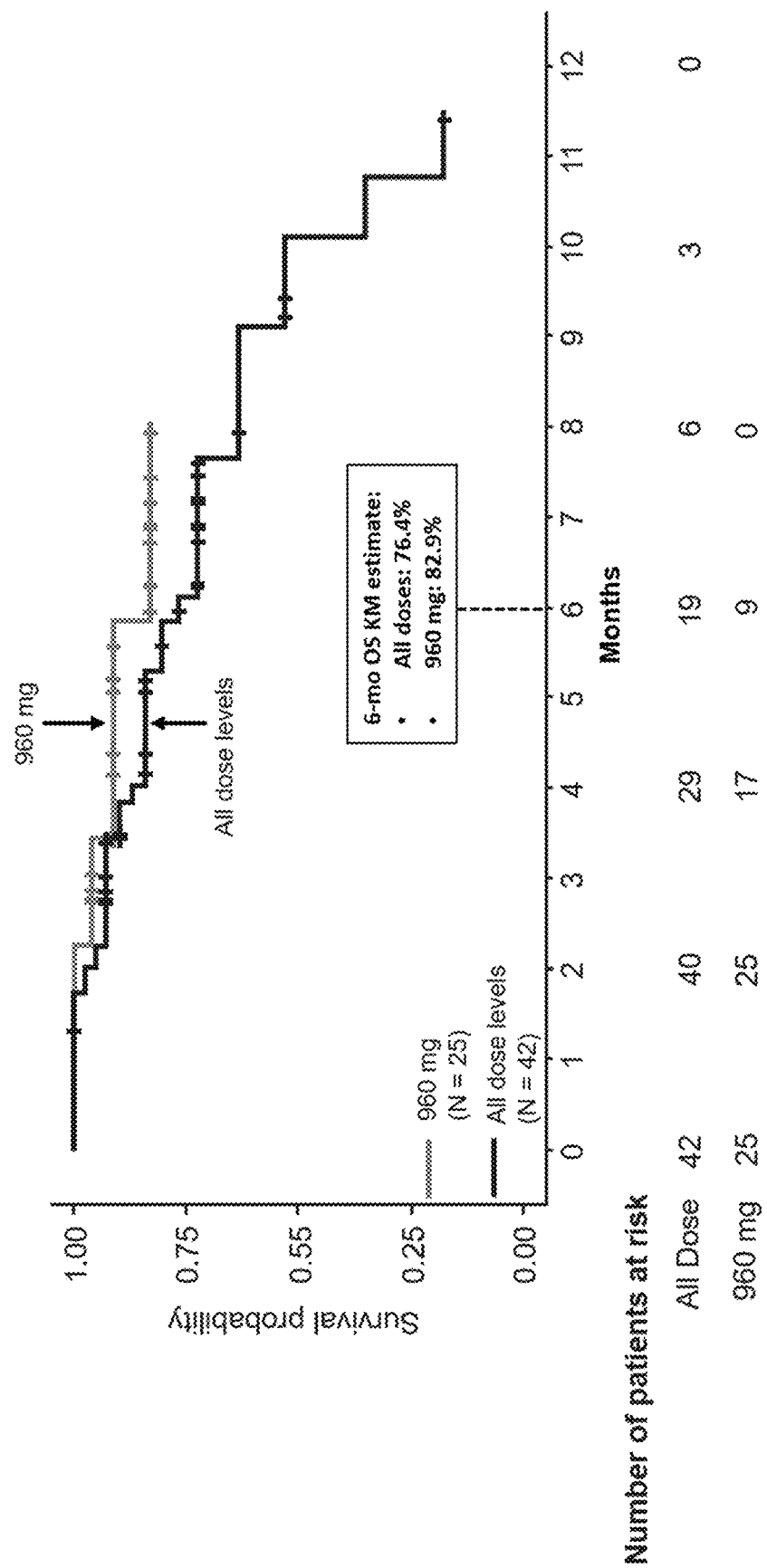
FIG. 9 shows the overall survival probability of patients with CRC.

The progression free survival (PFS) is shown in FIG. 8. The progression free survival at all dose levels was 4.0 months (median (min, max), 0.7, 11.0) and at 960 mg 4.2 months (median (min, max), 1.2, 5.7+; +: censored value). The 3-month and 6-month PFS rates for all doses were 58.5% and 20.6%, respectively. The 3-month PFS rate for the 960 mg total daily dose was 59.7%. The overall survival (OS) is shown in FIG. 9. The overall survival at all dose levels was 10.1 months (median (min, max), 1.3+, 11.4+; +: censored value; NR: not reached)) and at 960 mg NE (2.3, 8.0+). The 6-month OS rate was 76.4% for all doses and 82.9% for the 960 mg total daily dose.

Figure 10:
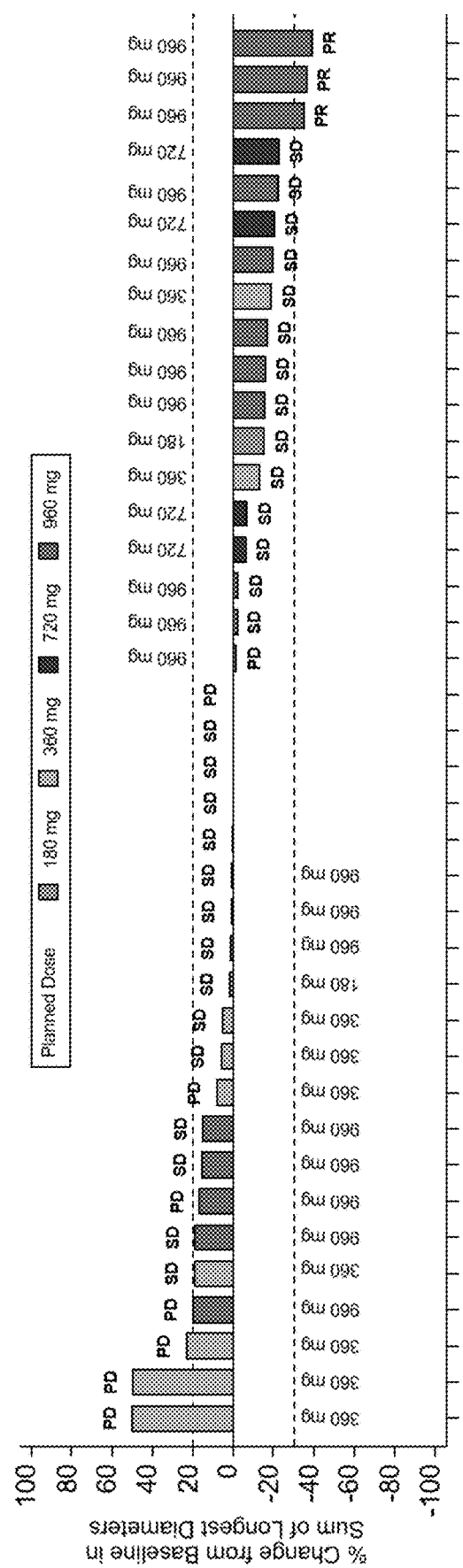
FIG. 10 shows the tumor burden in change from baseline for patients with CRC.
Figure 11:
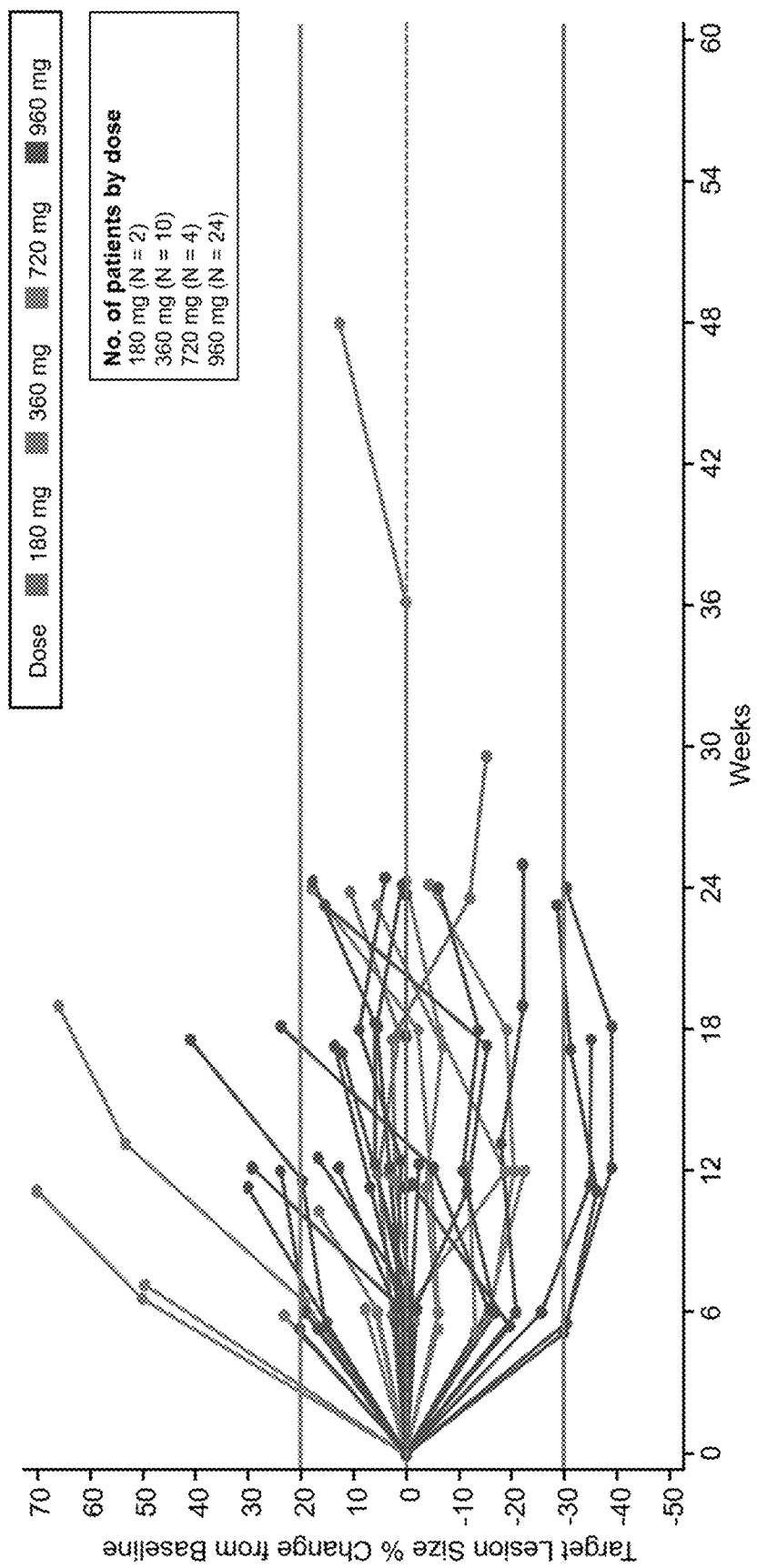
FIG. 11 shows the tumor burden change from baseline over time for patients with CRC over all four dosages of Compound A (180 mg, 360 mg, 720 mg, and 960 mg total daily dose).
Figure 12:
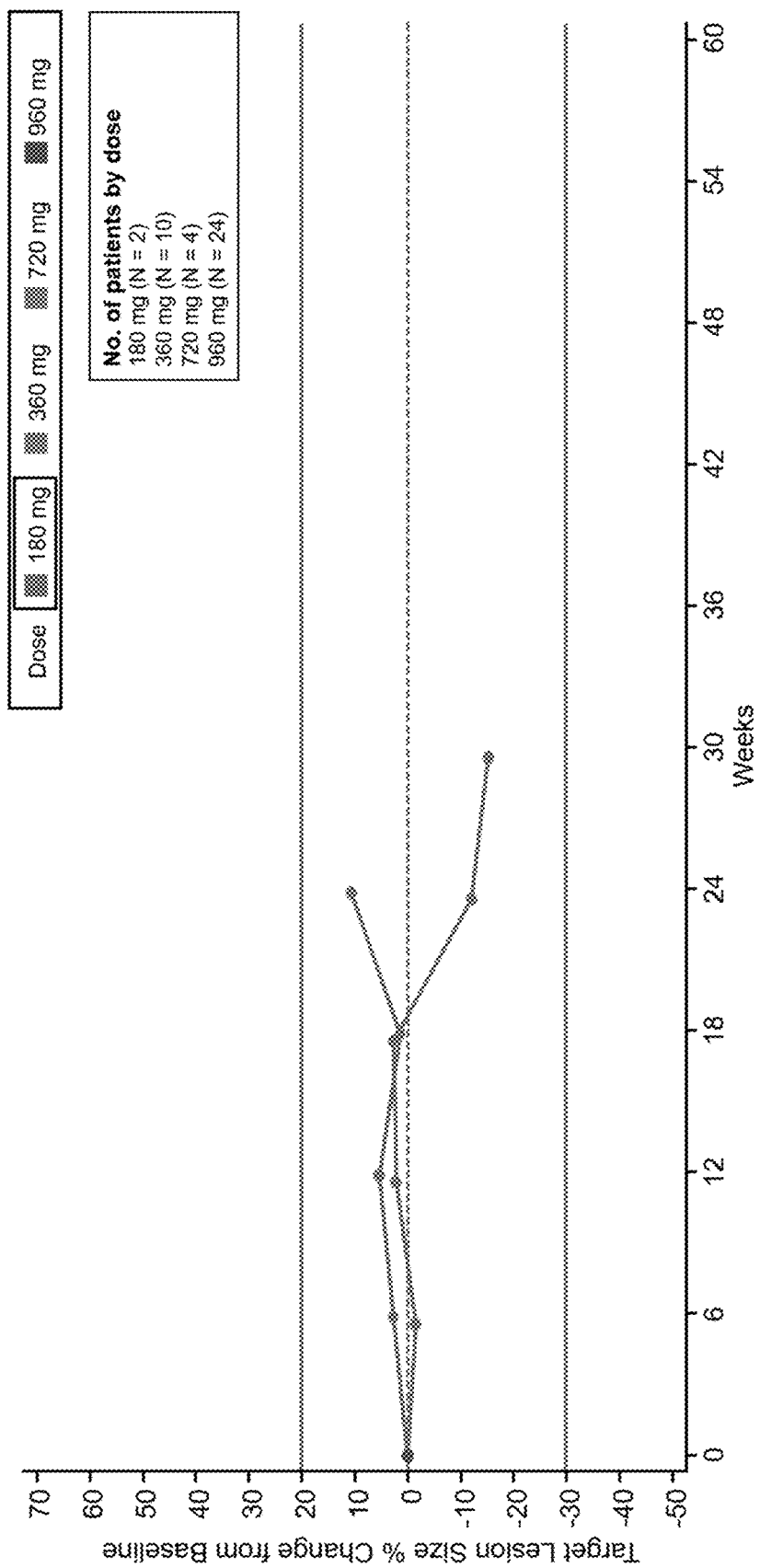
FIG. 12 shows the tumor burden change from baseline over time for a subset of patients with CRC shown in FIG. 11. Specifically.
Figure 13:
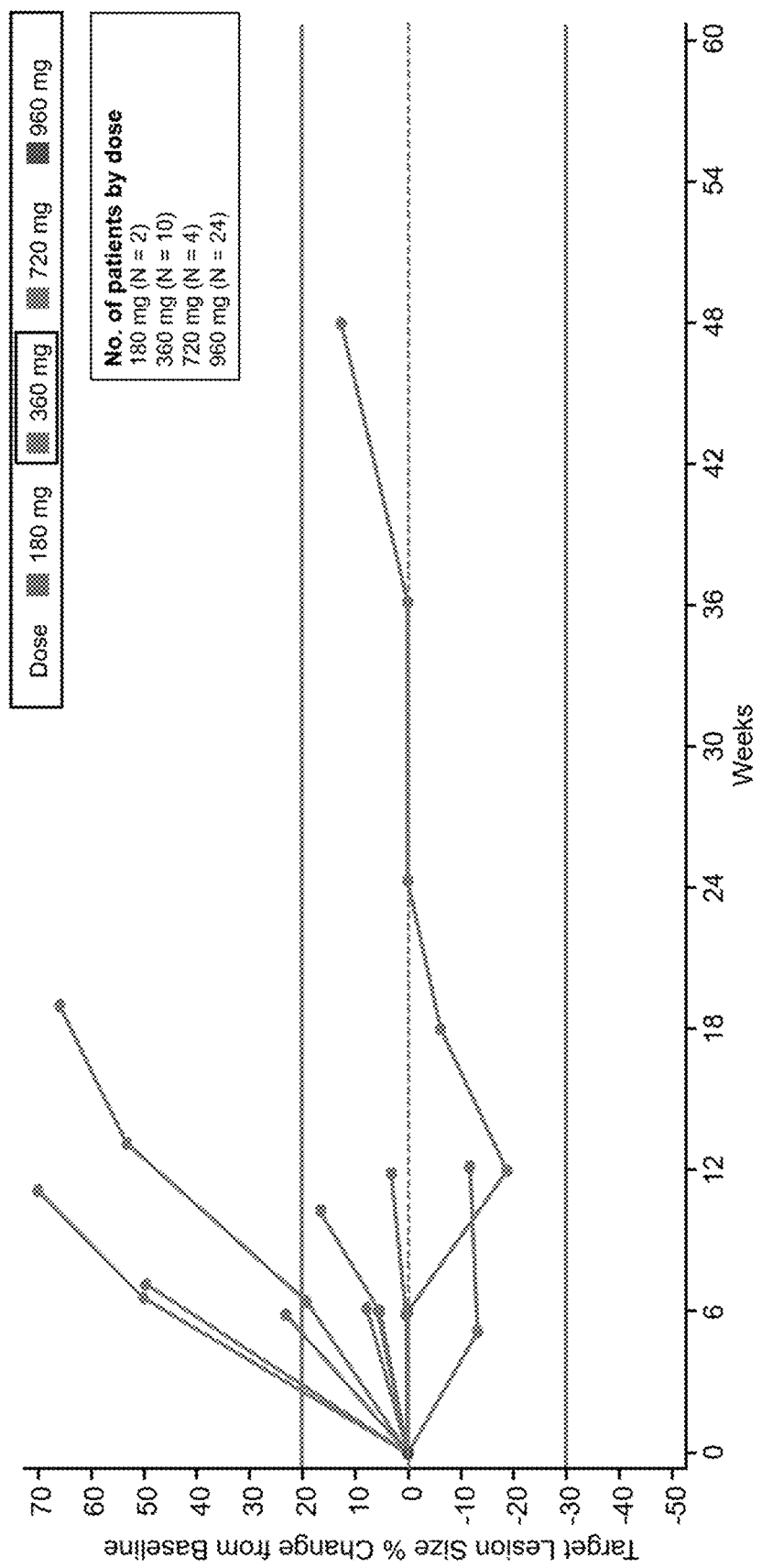
FIG. 13 shows the tumor burden change from baseline over time for a subset of patients with CRC shown in FIG. 11. Specifically.
Figure 14:
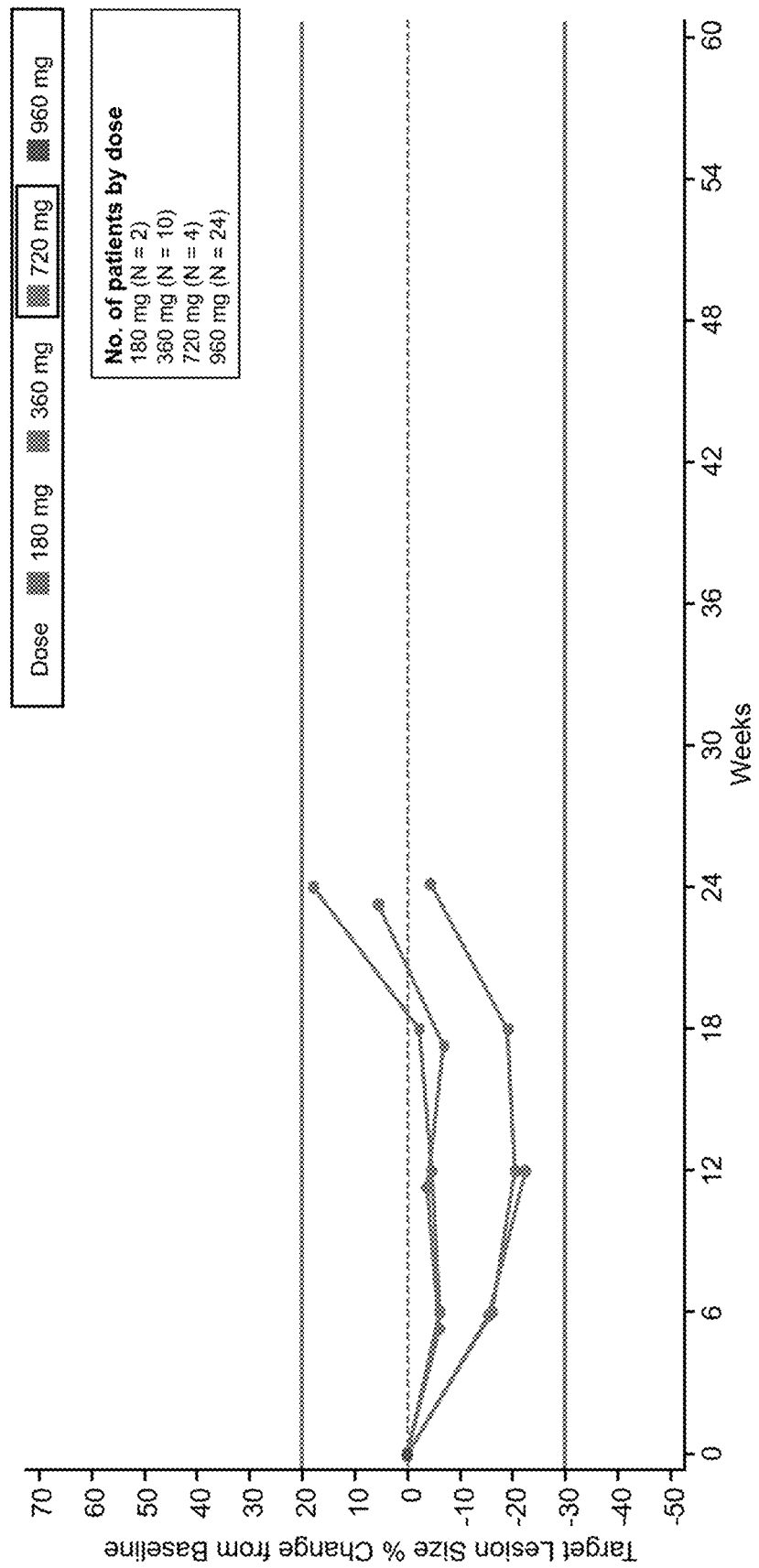
FIG. 14 shows the tumor burden change from baseline over time for a subset of patients with CRC shown in FIG. 11. Specifically.
Figure 15:
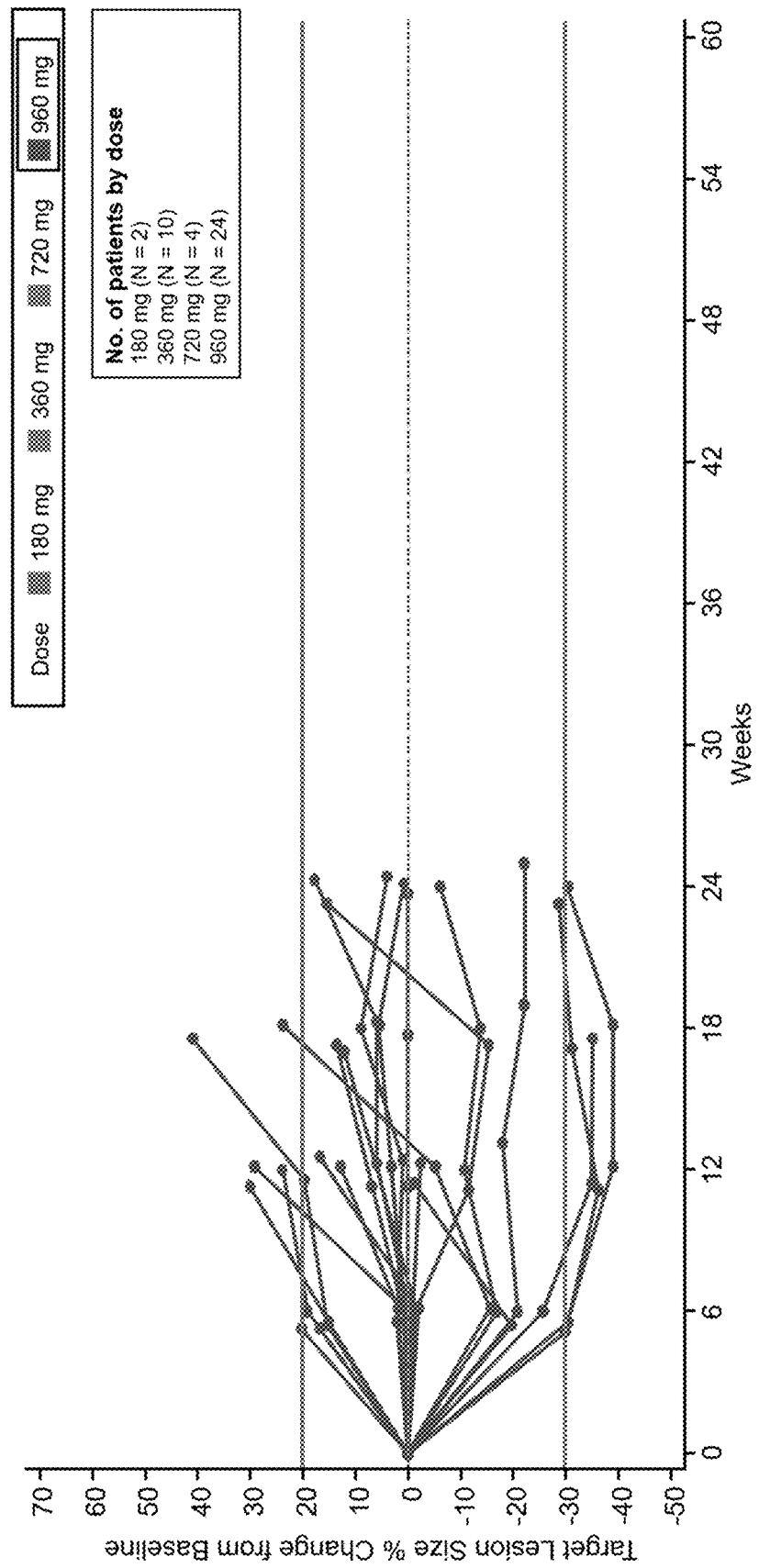
FIG. 15 shows the tumor burden change from baseline over time for a subset of patients with CRC shown in FIG. 11. Specifically.

The efficacy of Compound A in patients with CRC is shown in FIG. 10 (% change from baseline in sum of longest diameter v. evaluable CRC patients with available postbaseline tumor data (N=39). Three patients are not included in the graph of FIG. 10 due to missing postbaseline tumor data (1 PD, 1 SD, 1 not done with clinical progression).

FIGS. 11-15 show the tumor burden change from baseline over time for patients with CRC over all four dosages of Compound A (FIG. 11; 180 mg, 360 mg, 720 mg, and 960 mg total daily dose) and for individual dosages (FIGS. 12-15).

Figure 16:
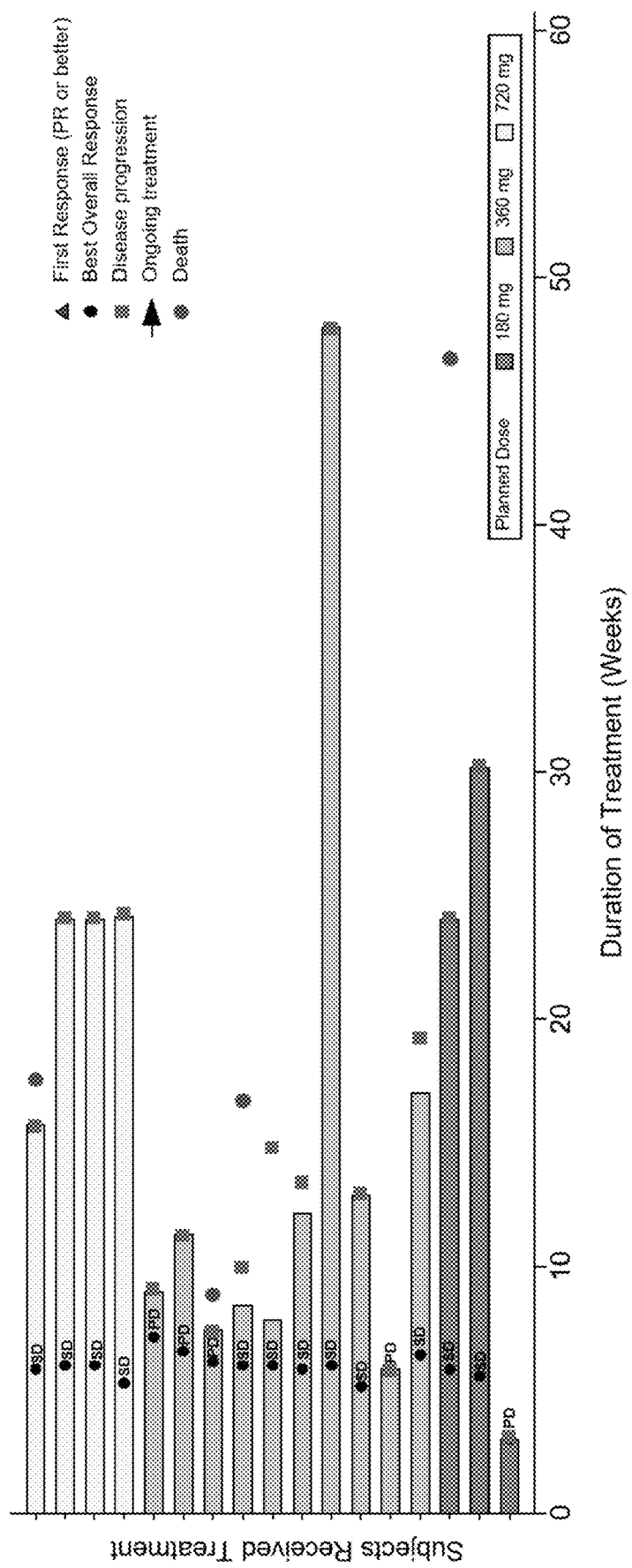
FIG. 16 shows the time to response and treatment over time for patients with CRC dosed with Compound A (counting from the top of the graph: bars 1-4 (720 mg), bars 5-14 (360 mg), and bars 15-17 (180 mg).
Figure 17:
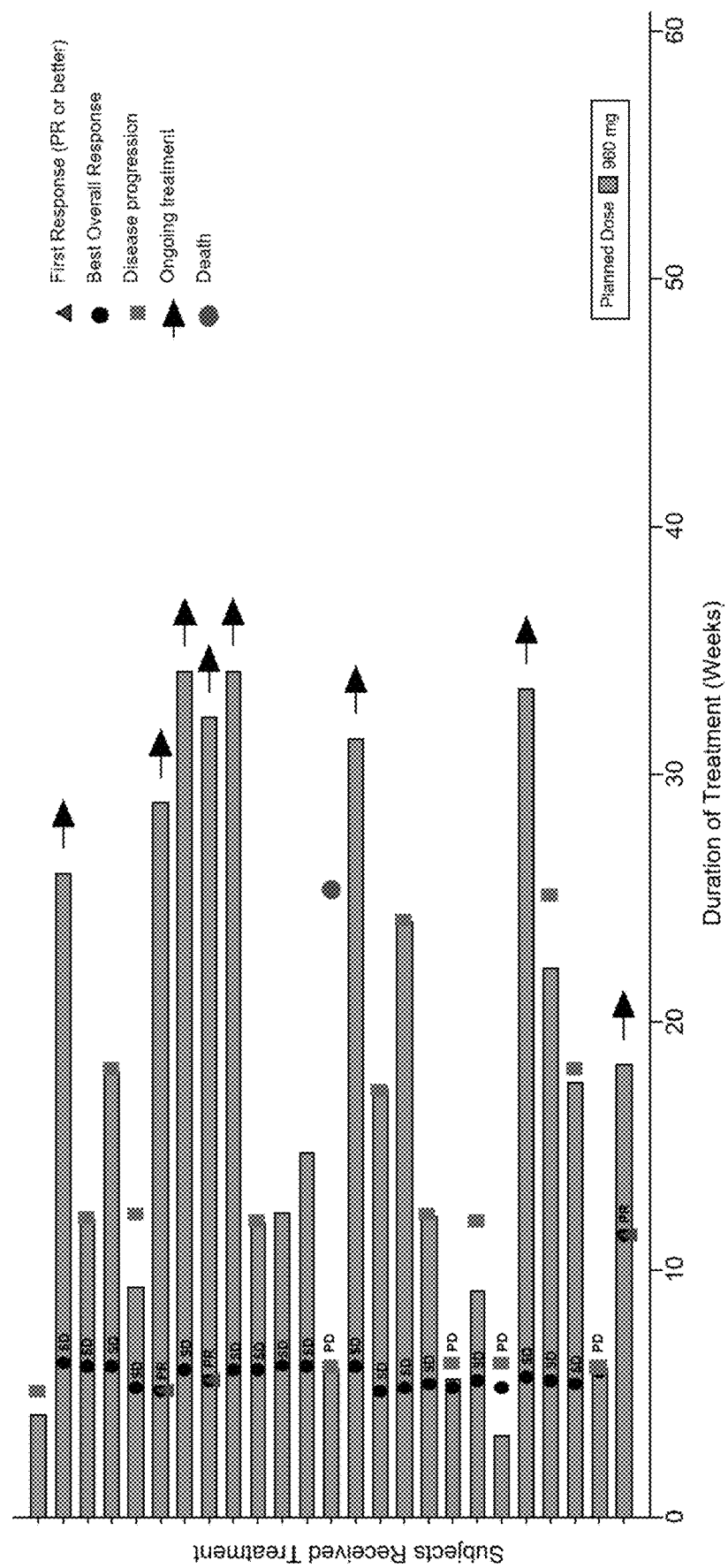
FIG. 17 shows the time to response and treatment over time for patients with CRC dosed with 960 mg of Compound A daily.

FIGS. 16 and 17 show the time to response and treatment over time for patients with CRC dosed with Compound A at various doses.

In conclusion, three of 42 patients (7.1%) with heavily pretreated KRAS p.G12C mutant metastatic CRC had durable partial responses to Compound A. In addition to the 3 responders, 29 patients achieved disease control, resulting in a disease control rate of 76.2% and a median progression-free survival (PFS) of 4.0 months (range: 0.7-11.0). Moreover, Compound A is well tolerated with mild treatment-related toxicities in CRC patients, consistent with previous results.

III. Patients With Advanced Solid Tumors Other Than NSCLC and CRC

By the cutoff date of Jan. 8, 2020, 25 patients with the following tumor types were enrolled: pancreatic cancer (10 patients), appendiceal cancer (4 patients), endometrial cancer (2 patients), unknown primary cancer (2 patients), bile duct cancer (1 patient), sinonasal cancer (1 patient), ampullary cancer (1 patient), small bowel cancer (1 patient), melanoma (1 patient), small cell lung cancer (1 patient), and esophageal cancer (1 patient). 2 appendiceal cancer patients received a total daily dose of 360 and 720 mg of Compound A, respectively. The remaining 23 patients received a total daily dose of 960 mg of Compound A. The median follow-up was 4.3 months (range: 0.1-12.6 months). 22 patients had been followed up for ≥7 weeks and were evaluable for response. By the cutoff date, 12 patients discontinued treatment, with disease progression as the most common cause. All enrolled patients had received prior lines of systemic anticancer therapy and 84% of enrolled patients received more than 1 prior line.

TABLE 12

Baseline Characteristics

| Baseline Characteristics | N = 25 |
|---|---|
| Median age (range) - year | 60.0 (40-75) |
| Female - n (%) | 9 (36.0) |
| ECOG performance status at baseline - n (%) | |
| 0 | 7 (28.0) |
| 1 | 14 (56.0) |
| 2 | 4 (16.0) |
| Prior lines of systematic anticancer therapy - n (%) | |
| 1 | 4 (16.0) |
| 2 | 5 (20.0) |
| 3 | 6 (24.0) |

TABLE 12-continued

Baseline Characteristics

| Baseline Characteristics | N = 25 |
|---|---|
| >3 | 9 (36.0) |
| Missing | 1 (4.0) |
| Number of prior systemic anticancer therapies - median (range) | 3 (1-4) |

ECOG = Eastern Cooperative Oncology Group

The following table summarizes the patient incidence of adverse events (AEs). The treatment-related TEAEs reported for more than one patient were diarrhea (2 out of 25 patients) and fatigue (2 out of 25 patients). The grade 3 treatment-related AEs reported were diarrhea (1 out of 25 patients) and pneumonia (1 out of 25 patients). There were no dose-limiting toxicities and no treatment-related adverse events leading to discontinuation. As discussed above, the 960 mg total daily dose of Compound A was identified as the expansion dose and recommended Phase 2 dose.

TABLE 13

Summary of Patient Incidence of Adverse Events (AEs)

| | All Treatment-Emergent AEs (TEAEs), N = 25, n (%) | All Treatment-Related TEAEs N = 25, n (%) |
|---|---|---|
| Any grade | 20 (80.0) | 9 (36.0) |
| Grade ≥2 | 17 (68.0) | 4 (16.0) |
| Grade ≥3 | 15 (60.0) | 2 (8.0) |
| Grade ≥4 | 4 (16.0) | 0 (0.0) |
| Dose-limiting toxicities | 0 (0.0) | 0 (0.0) |
| Serious AEs | 13 (52.0) | 1 (4.0) |
| Fatal AEs | 4 (16.0) | 0 (0.0) |
| AEs leading to treatment discontinuation | 3 (12.0) | 0 (0.0) |

AE: adverse event

The tumor response of these patients is reported in the table below. 22 patients were evaluable for tumor response. 3 had confirmed partial response, 13 had stable disease, and 6 had disease progression. The 3 partial responders had appendiceal cancer, melanoma, and endometrial cancer, respectively. 13 patients achieving stable disease included 6 with pancreatic cancer, 2 with appendiceal cancer, 1 with ampullary cancer, 1 with bile duct cancer, 1 with endometrial cancer, 1 with sinonasal cancer, and 1 with unknown primary. 3 Patients with pancreatic cancer achieving stable disease had close to 30% reduction by RECIST 1.1.

TABLE 14

Tumor Response

| Best Tumor Response | Evaluable patients, N = 22 |
|---|---|
| Confirmed partial response - n | 3 |
| Tumor types (n) | Appendiceal (1) |
| | Melanoma (1) |
| | Endometrial (1) |
| Stable disease - n | 13 |
| Tumor types (n) | Pancreatic (6) |
| | Appendiceal (2) |
| | Ampullary (1) |
| | Bile duct (1) |
| | Endometrial (1) |
| | Sinonasal (1) |
| | Unknown primary (1) |

TABLE 14-continued

Tumor Response

| Best Tumor Response | Evaluable patients, N = 22 |
|---|---|
| Progressive disease - n | 6 |
| Tumor types (n) | Pancreatic (2) |
|  | Appendiceal (1) |
|  | Small cell lung cancer (1) |
|  | Esophageal (1) |
|  | Small bowel cancer (1) |

Figure 18:
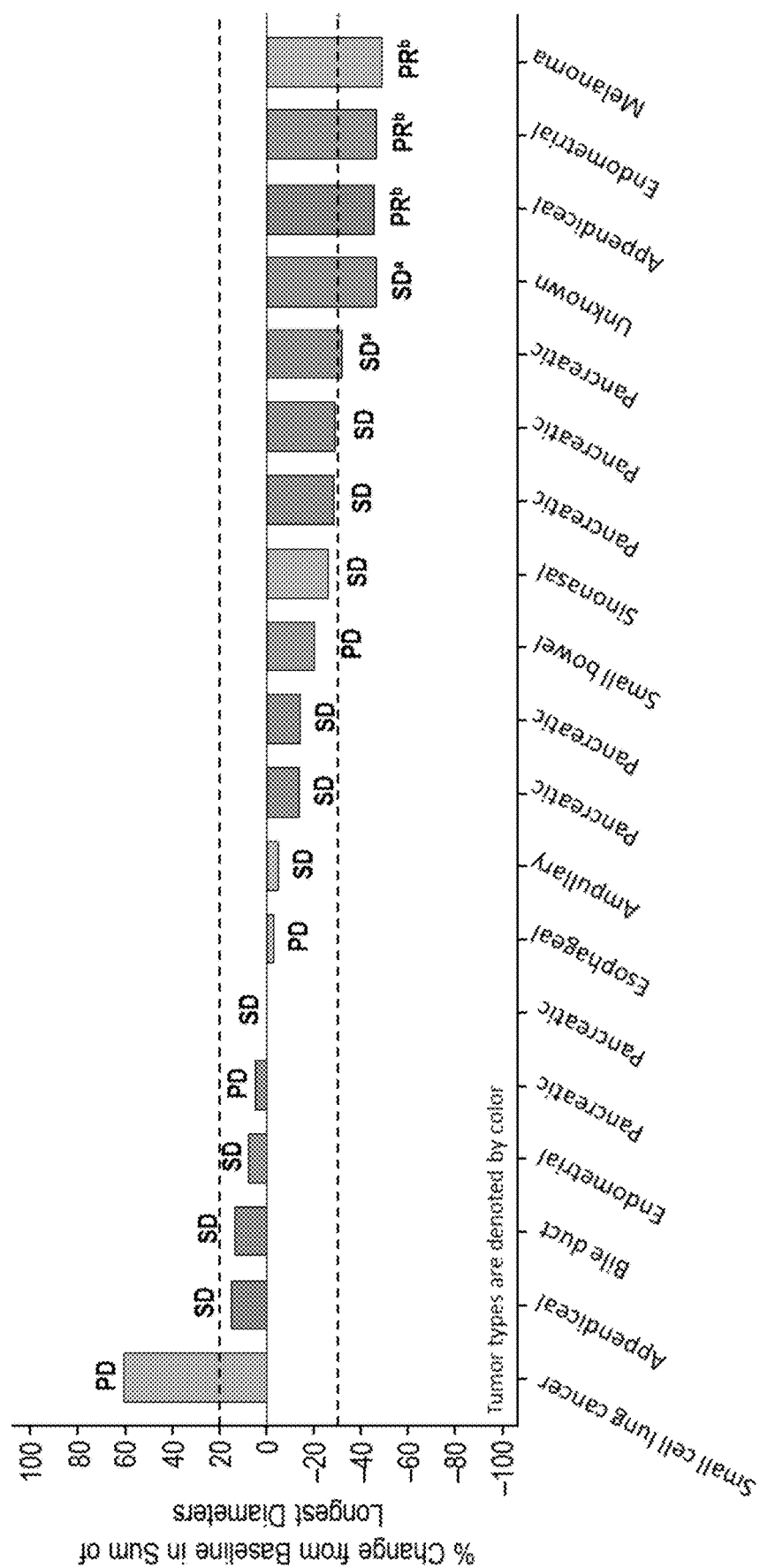
FIG. 18 shows the efficacy of Compound A in patients with advanced solid tumors other than NSCLC and CRC as change in tumor burden from baseline. The superscript "a" on certain bars indicated that patients had unconfirmed PR. The superscript "b" on certain three bars marked PR indicates that one patient with appendiceal cancer received a 720 mg total daily dose of Compound A and the other two patients (endometrial cancer and melanoma) received each a 960 mg total daily dose of Compound A.

The efficacy of Compound A in these patients is shown in FIG. 18 (% change from baseline in sum of longest diameter v. evaluable patients with available post-baseline tumor data (N=19). Three patients are not included in the graph of FIG. 18 due to missing postbaseline tumor data (2 appendiceal patients (1 PD, 1 SD,) and one pancreatic patient (PD).

Figure 19:
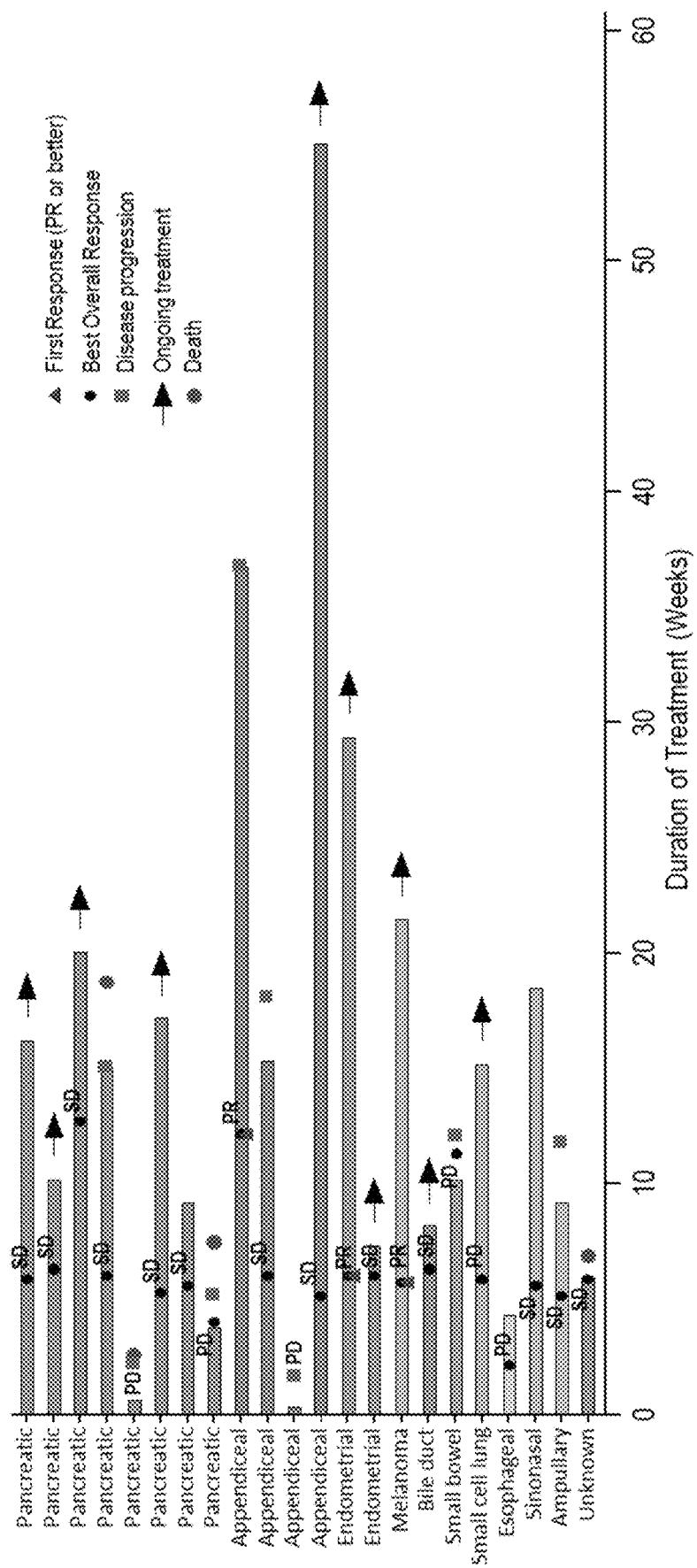
FIG. 19 shows the time to response and treatment over time for patients with advanced solid tumors other than NSCLC and CRC.

FIG. 19 shows the time to response and treatment over time for these patients.

In conclusion, encouraging anticancer activity in multiple tumor types with KRAS G12C has been observed. A confirmed partial response was observed in 3 patients with appendiceal cancer, melanoma, and endometrial cancer, respectively. 6 of the 8 evaluable patients with pancreatic cancer achieved stable disease—three of them had 30% reduction of tumor burden. The toxicities associated with Compound A were mild and manageable, consistent with previous results.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed:

1. A method of treating KRAS G12C-mutated locally advanced or metastatic non-small cell lung cancer in a subject in need thereof, comprising orally administering to the subject 960 mg once daily of a compound, wherein the compound is

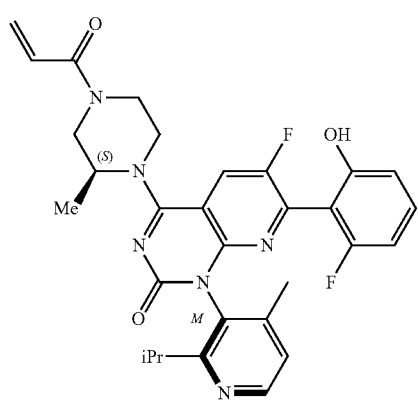

2. The method of claim 1, wherein the subject, prior to first administering the compound, has undergone at least one systemic cancer therapy.

3. The method of claim 1, wherein the compound is administered as a tablet.

4. The method of claim 2, wherein the compound is administered as a tablet.

5. The method of claim 1, wherein the subject is an adult.

6. The method of claim 2, wherein the subject is an adult.

7. The method of claim 3, wherein the subject is an adult.

8. The method of claim 4, wherein the subject is an adult.

9. A method of treating KRAS G12C-mutated non-small cell lung cancer in a subject in need thereof, comprising administering to the subject 960 mg once daily of a compound, wherein the compound is

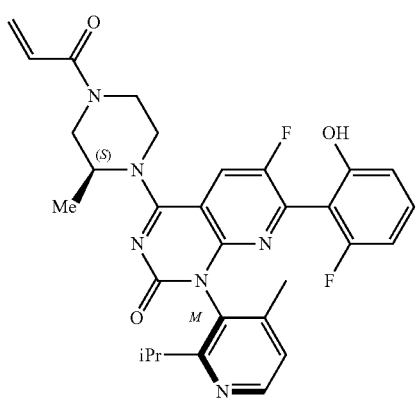

10. The method of claim 9, wherein the subject, prior to first administering the compound, has undergone at least one systemic cancer therapy.

11. The method of claim 9, wherein the compound is administered as a tablet.

12. The method of claim 10, wherein the compound is administered as a tablet.

13. The method of claim 11, wherein the compound is administered orally.

14. The method of claim 12, wherein the compound is administered orally.

15. The method of claim 9, wherein the subject is an adult.

16. The method of claim 10, wherein the subject is an adult.

17. The method of claim 11, wherein the subject is an adult.

18. The method of claim 12, wherein the subject is an adult.

19. The method of claim 13, wherein the subject is an adult.

20. The method of claim 14, wherein the subject is an adult.

21. A method of treating KRAS G12C-mutated colorectal cancer in a subject in need thereof, comprising administering to the subject 960 mg once daily of a compound, wherein the compound is

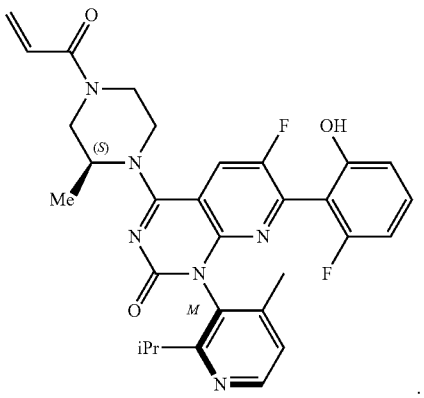

22. The method of claim 21, wherein the subject, prior to first administering the compound, has undergone at least one systemic cancer therapy.
23. The method of claim 21, wherein the subject, prior to first administering the compound, has undergone at least two systemic cancer therapies.
24. The method of claim 21, wherein the compound is administered as a tablet.
25. The method of claim 22, wherein the compound is administered as a tablet.
26. The method of claim 23, wherein the compound is administered as a tablet.
27. The method of claim 24, wherein the compound is administered orally.
28. The method of claim 25, wherein the compound is administered orally.
29. The method of claim 26, wherein the compound is administered orally.
30. The method of claim 21, wherein the subject is an adult.
31. The method of claim 22, wherein the subject is an adult.
32. The method of claim 23, wherein the subject is an adult.
33. The method of claim 24, wherein the subject is an adult.
34. The method of claim 25, wherein the subject is an adult.
35. The method of claim 26, wherein the subject is an adult.
36. A method of treating KRAS G12C-mutated pancreatic cancer in a subject in need thereof, comprising administering to the subject 960 mg once daily of a compound, wherein the compound is

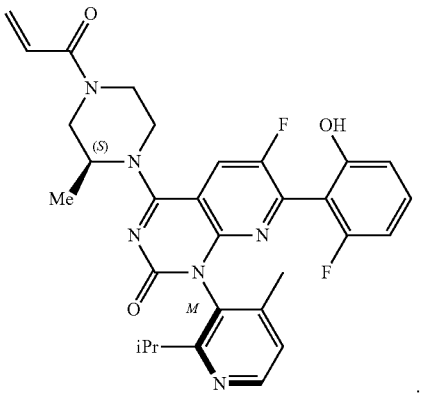

37. The method of claim 36, wherein the subject, prior to first administering the compound, has undergone at least one systemic cancer therapy.
38. The method of claim 36, wherein the compound is administered as a tablet.
39. The method of claim 37, wherein the compound is administered as a tablet.
40. The method of claim 38, wherein the compound is administered orally.
41. The method of claim 39, wherein the compound is administered orally.
42. The method of claim 36, wherein the subject is an adult.
43. The method of claim 37, wherein the subject is an adult.
44. The method of claim 38, wherein the subject is an adult.
45. The method of claim 39, wherein the subject is an adult.
46. The method of claim 40, wherein the subject is an adult.
47. The method of claim 41, wherein the subject is an adult.

* * * * *

UNITED STATES PATENT AND TRADEMARK OFFICE
CERTIFICATE OF CORRECTION

| | | |
|---|---|---|
| PATENT NO. | : 11,426,404 B2 | Page 1 of 1 |
| APPLICATION NO. | : 15/930606 | |
| DATED | : August 30, 2022 | |
| INVENTOR(S) | : Henary et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
Twenty-first Day of January, 2025

Coke Morgan Stewart
*Acting Director of the United States Patent and Trademark Office*